US011684703B2

(12) United States Patent
Adams et al.

(10) Patent No.: US 11,684,703 B2
(45) Date of Patent: Jun. 27, 2023

(54) COATINGS FOR IMPLANTABLE DEVICES

(71) Applicant: QURA, INC., Sudbury, MA (US)

(72) Inventors: Douglas P. Adams, Sudbury, MA (US); Amitava Gupta, Roanoke, VA (US)

(73) Assignee: Qura, Inc., Duxbury, MA (US)

( * ) Notice: Subject to any disclaimer, the term of this patent is extended or adjusted under 35 U.S.C. 154(b) by 182 days.

(21) Appl. No.: 16/971,489

(22) PCT Filed: Feb. 20, 2019

(86) PCT No.: PCT/US2019/018764
§ 371 (c)(1),
(2) Date: Aug. 20, 2020

(87) PCT Pub. No.: WO2019/164940
PCT Pub. Date: Aug. 29, 2019

(65) Prior Publication Data
US 2021/0052783 A1   Feb. 25, 2021

Related U.S. Application Data

(60) Provisional application No. 62/634,578, filed on Feb. 23, 2018, provisional application No. 62/632,574, filed on Feb. 20, 2018.

(51) Int. Cl.
A61L 31/10 (2006.01)
A61L 31/16 (2006.01)
A61L 33/06 (2006.01)
A61B 3/16 (2006.01)
A61L 33/00 (2006.01)

(52) U.S. Cl.
CPC ............... A61L 31/10 (2013.01); A61B 3/16 (2013.01); A61L 31/16 (2013.01); A61L 33/0011 (2013.01); A61L 33/068 (2013.01); A61B 2562/0247 (2013.01); A61B 2562/16 (2013.01); A61L 2300/204 (2013.01); A61L 2300/222 (2013.01); A61L 2300/41 (2013.01); A61L 2300/42 (2013.01); A61L 2300/426 (2013.01); A61L 2300/434 (2013.01); A61L 2400/04 (2013.01); A61L 2420/08 (2013.01)

(58) Field of Classification Search
None
See application file for complete search history.

(56) References Cited

U.S. PATENT DOCUMENTS

| 4,834,750 | A | | 5/1989 | Gupta | |
|---|---|---|---|---|---|
| 5,037,435 | A | * | 8/1991 | Chang | B29C 39/006 264/1.36 |
| 5,821,306 | A | * | 10/1998 | Hodd | G02B 1/043 525/228 |
| 5,834,070 | A | * | 11/1998 | Movchan | C23C 14/027 427/126.3 |
| 8,475,374 | B2 | | 7/2013 | Irazoqui et al. | |
| 9,078,613 | B2 | | 7/2015 | Irazoqui et al. | |
| 9,173,564 | B2 | | 11/2015 | Choo et al. | |
| 9,596,988 | B2 | | 3/2017 | Irazoqui et al. | |
| 9,662,021 | B2 | | 5/2017 | Chow et al. | |
| 10,044,227 | B2 | | 8/2018 | Chappell et al. | |
| 10,426,341 | B2 | | 10/2019 | Choo et al. | |
| 2009/0043384 | A1 | * | 2/2009 | Niwa | A61F 2/1648 623/6.13 |
| 2010/0055769 | A1 | * | 3/2010 | Kurt | G01N 33/6803 422/240 |
| 2010/0068141 | A1 | * | 3/2010 | Kaushal | A61P 27/02 606/4 |
| 2010/0137694 | A1 | | 6/2010 | Irazoqui et al. | |
| 2013/0090534 | A1 | * | 4/2013 | Burns | G16H 10/60 600/398 |
| 2014/0016087 | A1 | | 1/2014 | Gupta et al. | |
| 2017/0164831 | A1 | | 6/2017 | Choo et al. | |
| 2017/0209045 | A1 | | 7/2017 | Choo et al. | |
| 2018/0035888 | A1 | | 2/2018 | Irazoqui et al. | |
| 2018/0375382 | A1 | | 12/2018 | Chappell et al. | |
| 2019/0175015 | A1 | * | 6/2019 | Adams | A61L 31/145 |
| 2020/0237218 | A1 | | 7/2020 | Irazoqui et al. | |

FOREIGN PATENT DOCUMENTS

| WO | WO-9858990 A1 | * | 12/1998 | ........... A61L 29/085 |
|---|---|---|---|---|
| WO | 2000022460 A1 | | 4/2000 | |
| WO | 2008134573 A1 | | 11/2008 | |
| WO | 2010093873 A2 | | 8/2010 | |
| WO | 2013090886 A1 | | 6/2013 | |

(Continued)

OTHER PUBLICATIONS

Yoshida et al. Applied Optics 1996 3(9):1500-1506 (Year: 1996).*
Nguyen et al. European Polymer Journal 2013 49(12):4201-4211 (Year: 2013).*
Chan et al. Langmuir 2005 21(19):8930-8939 (Year: 2005).*
Ferreira et al. International Journal of Pharmaceutics 2000 194:169-180 (Year: 2000).*
Araci et al., "An implantable microfluidic device for self-monitoring of intraocular pressure." Nature medicine 20.9 (2014): 1074-1078.
Chen et al., "Implantable parylene-based wireless intraocular pressure sensor." 2008 IEEE 21st International Conference on Micro Electro Mechanical Systems. IEEE, 2008. 4 pages.

(Continued)

Primary Examiner — Melissa S Mercier
Assistant Examiner — Caralynne E Helm
(74) Attorney, Agent, or Firm — Smith Baluch LLP

(57) ABSTRACT

Intraocular pressure sensors, systems, and methods of use. Implantable intraocular pressure sensing devices that are hermetically sealed and adapted to wirelessly communicate with an external device. The implantable devices can include a hermetically sealed housing, the hermetically sealed housing including therein: an antenna in electrical communication with a rechargeable power source, the rechargeable power source in electrical communication with an ASIC, and the ASIC in electrical communication with a pressure sensor.

20 Claims, 15 Drawing Sheets

(56) References Cited

FOREIGN PATENT DOCUMENTS

| WO | 2017210316 A1 | 12/2017 |
| WO | 2019164940 A1 | 8/2019 |
| WO | 2019191748 A1 | 10/2019 |
| WO | 2019216945 A1 | 11/2019 |
| WO | 2020023036 A1 | 1/2020 |
| WO | 2020046299 A1 | 3/2020 |
| WO | 2020081072 A1 | 4/2020 |
| WO | 2020160262 A1 | 8/2020 |
| WO | 2020236139 A1 | 11/2020 |

OTHER PUBLICATIONS

Chen et al., "Microfabricated implantable parylene-based wireless passive intraocular pressure sensors." Journal of Microelectromechanical Systems 17.6 (2008): 1342-1351.

Dziki et al., "Extracellular matrix bioscaffolds as immunomodulatory biomaterials." Tissue Engineering Part A 23.19-20 (2017): 1152-1159.

Eldred et al., "The lens as a model for fibrotic disease." Philosophical Transactions of the Royal Society B: Biological Sciences 366.1568 (2011): 1301-1319.

Eye Diseases Prevalence Research Group. "Prevalence of open-angle glaucoma among adults in the United States." Archives of ophthalmology 122.4 (2004): 532. 16 pages.

EYEMATE—novel implant for monitoring glaucoma (neuartiges Implantat zur Überwachung des Glaukoms) with machine translatoin. Implandata Ophthalmic Products GmbH 2015. Accessed at https://infocenter.my-eyemate.com/pdf/InForm_1_2015_IOP.pdf. 3 pages.

Gandhi et al., "Studies on thermoresponsive polymers: Phase behaviour, drug delivery and biomedical applications." asian journal of pharmaceutical sciences 10.2 (2015): 99-107.

Gharib et al., "Liposomes incorporating cyclodextrin-drug inclusion complexes: Current state of knowledge." Carbohydrate polymers 129 (2015): 175-186.

Ha et al., "Polymer-based miniature flexible capacitive pressure sensor for intraocular pressure (IOP) monitoring inside a mouse eye." Biomedical microdevices 14.1 (2012): 207-215.

Haque et al., "An intraocular pressure sensor based on a glass reflow process." Solid-State Sensors, Actuators, and Microsystems Workshop. Hilton Head Island, 2010. 4 pages.

Hastings et al., "An Implantable, All-Optical Sensor for Intraocular Pressure Monitoring." Investigative Ophthalmology & Visual Science 53.14 (2012): 5039-5039.

Hirayama et al., "Permeation properties to CO2 and N2 of poly (ethylene oxide)-containing and crosslinked polymer films" Journal of Membrane Science 160.1 (1999): 87-99.

Kim et al., "Preliminary study on implantable inductive-type sensor for continuous monitoring of intraocular pressure." Clinical & experimental ophthalmology 43.9 (2015): 830-837.

Koley et al., "Miniaturized implantable pressure and oxygen sensors based on polydimethylsiloxane thin films." Materials Science and Engineering: C 29.3 (2009): 685-690.

Mariacher et al., "Investigation of a novel implantable suprachoroidal pressure transducer for telemetric intraocular pressure monitoring." Experimental eye research 151 (2016): 54-60.

Melki et al., "An implantable intraocular pressure transducer: initial safety outcomes." JAMA ophthalmology 132.10 (2014): 1221-1225.

Neitz, A small ring that watches over the eye (Ein kleiner Ring, der über das Auge wacht) with machine translation. Service Oct. 2011. 4 pages.

New devices and technology take IOP monitoring to next level. Ophthalmology Times Feb. 8, 2014. Accessed at https://www.ophthalmologytimes.com/view/new-devices-and-technology-take-iop-monitoring-next-level on Apr. 29, 2021. 2 pages.

Optical implant and app could catch early signs of glaucoma. CTV News Aug. 4, 2014. Accessed at https://www.ctvnews.ca/health/optical-implant-and-app-could-catch-early-signs-of-glaucoma-1.1945468 on Apr. 29, 2021. 3 pages.

Paschalis et al., "Reliable intraocular pressure measurement using automated radio-wave telemetry." Clinical Ophthalmology (Auckland, NZ) 8 (2014): 177. 9 pages.

Piffaretti et al., "Rollable and implantable intraocular pressure sensor for the continuous adaptive management of glaucoma." 2013 35th Annual International Conference of the IEEE Engineering in Medicine and Biology Society (EMBC). IEEE, 2013. 5 pages.

Pintwala, Development of an in vitro model to assess wound-healing response and biocompatibility of intraocular biomaterials. MS thesis. University of Waterloo, 2014. 120 pages.

Quigley et al., "The number of people with glaucoma worldwide in 2010 and 2020." British journal of ophthalmology 90.3 (2006): 262-267.

Suske, Microsensor in the eye. Informationsdienst Wissenschaft May 26, 2014. Accessed at https://idw-online.de/en/news588835 on Apr. 29, 2021. 2 pages.

The Solution: eyemate®. Implandata Ophthalmic Products GmbH. Accessed at https://www.implandata.com/EN/solution-eyemate.html on Apr. 29, 2021. 3 pages.

Todani et al., "Intraocular pressure measurement by radio wave telemetry." Investigative ophthalmology & visual science 52.13 (2011): 9573-9580.

Wallace et al., "A tissue sealant based on reactive multifunctional polyethylene glycol." Journal of Biomedical Materials Research: An Official Journal of The Society for Biomaterials, The Japanese Society for Biomaterials, and The Australian Society for Biomaterials and the Korean Society for Biomaterials 58.5 (2001): 545-555.

Yu et al., "Chronically implanted pressure sensors: challenges and state of the field." Sensors 14.11 (2014): 20620-20644.

Yung et al., "An overview of home tonometry and telemetry for intraocular pressure monitoring in humans." Graefe's Archive for Clinical and Experimental Ophthalmology 252.8 (2014): 1179-1188.

International Search Report and Written Opinion in International Patent Application No. PCT/US2019/018764 dated May 6, 2019, 20 pages.

Kompella et al., "Delivery of celecoxib for treating diseases of the eye: influence of pigment and diabetes." Expert opinion on drug delivery 7.5 (2010): 631-645.

Siatiri et al., "Intracameral tissue plasminogen activator to prevent severe fibrinous effusion after congenital cataract surgery." British journal of ophthalmology 89.11 (2005): 1458-1461.

Stahnke et al., "Suppression of TGF-β pathway by pirfenidone decreases extracellular matrix deposition in ocular fibroblasts in vitro." PLoS One 12.2 (2017): e0172592. 20 pages.

* cited by examiner

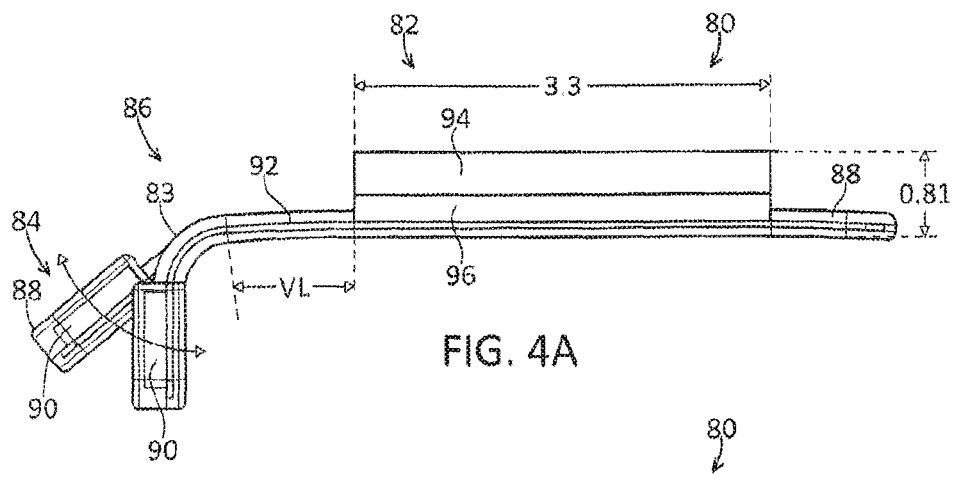
FIG. 4A
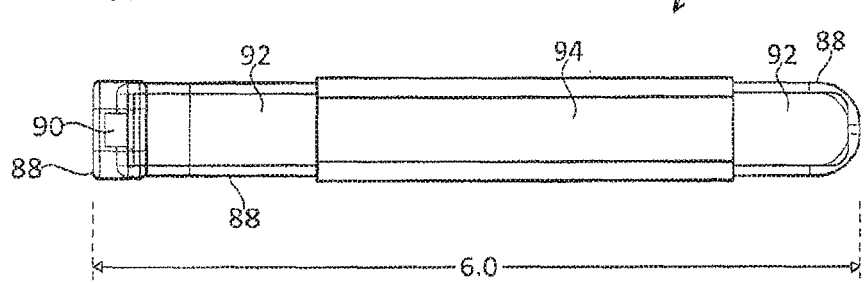
FIG. 4B
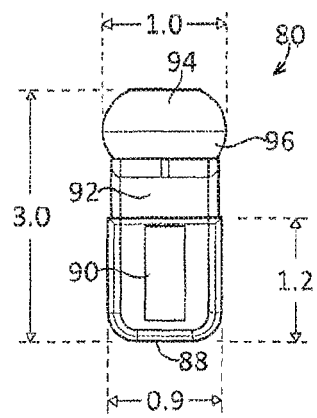
FIG. 4C  DIMENSIONS IN mm

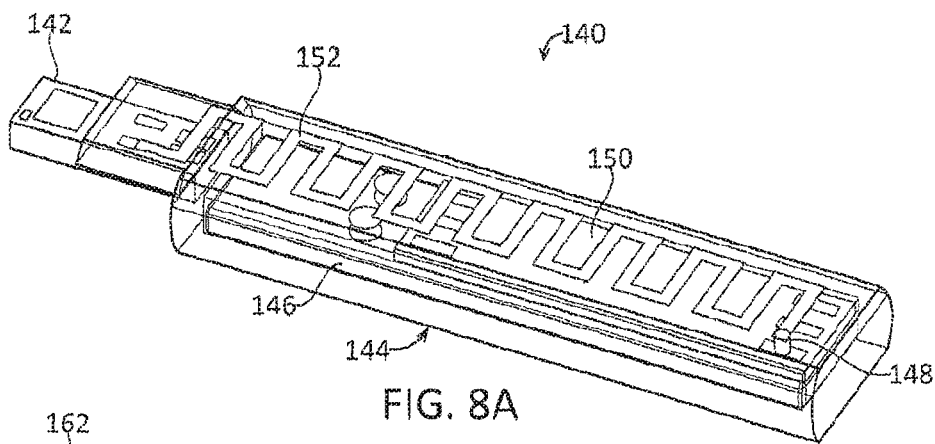
FIG. 8A
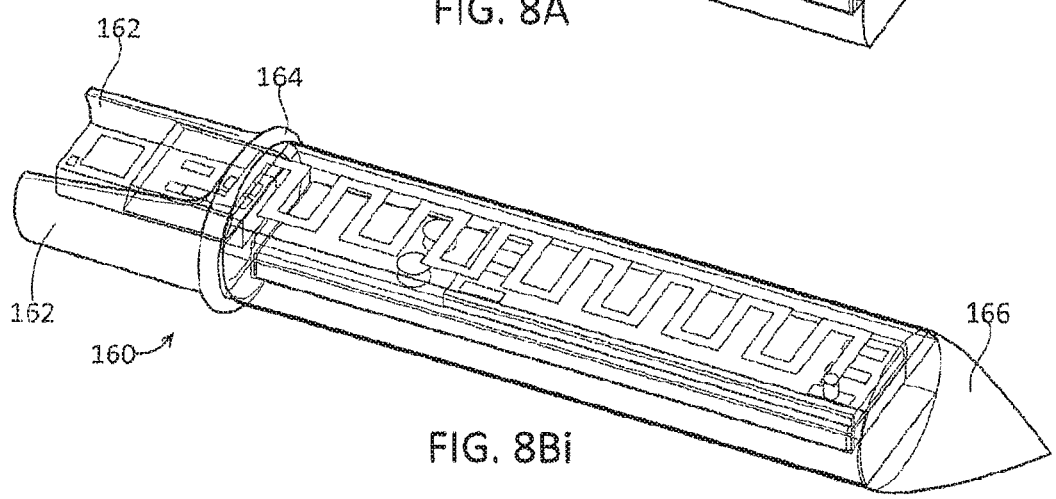
FIG. 8Bi
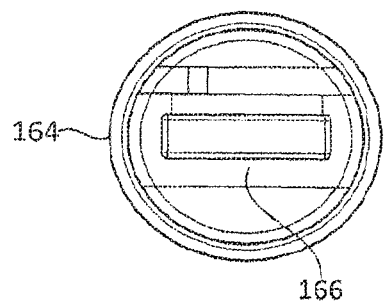
FIG. 8Bii

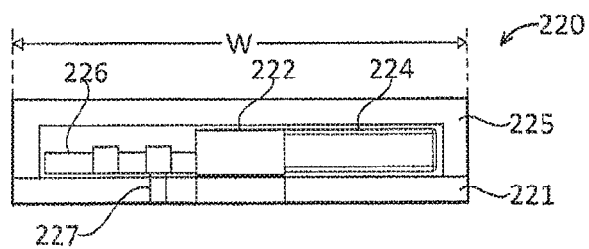
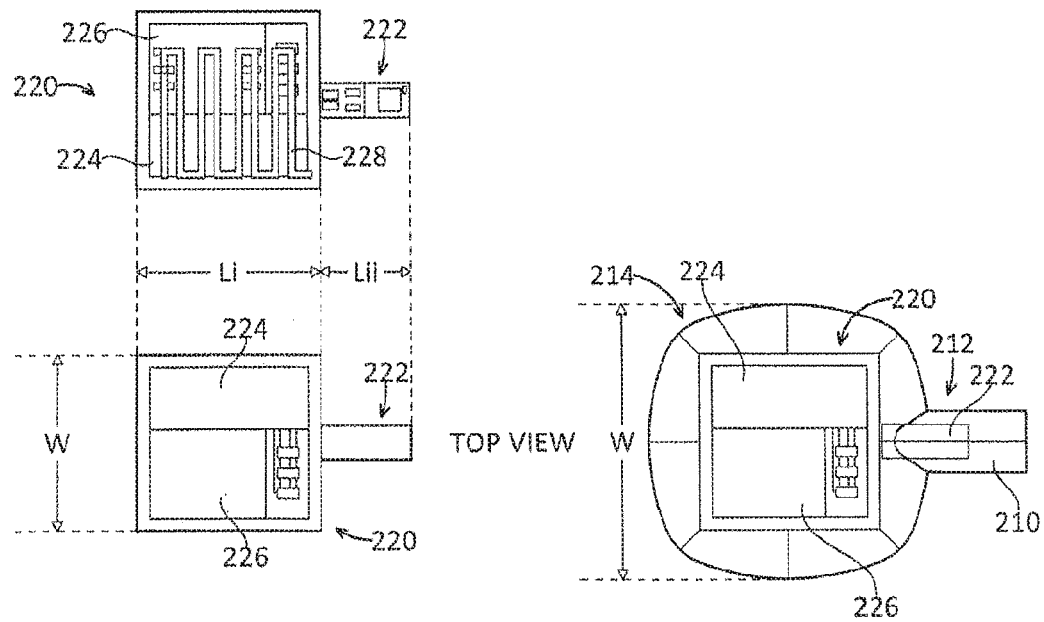
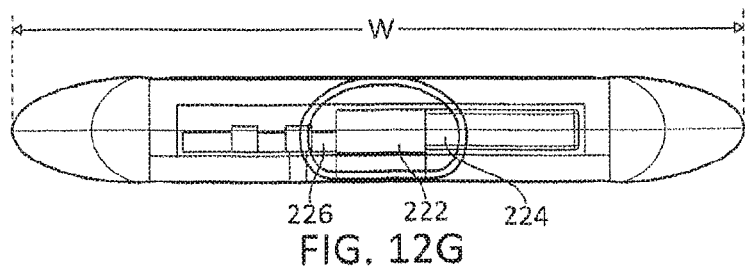
FIG. 12G

AN AMPHIPHILIC COATING WITH INFUSED OR WEAKLY BONDED ANTICOAGULANTS

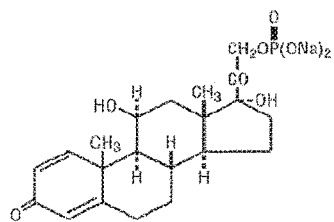
Figure 17 Molecular structure of Prednisolone.
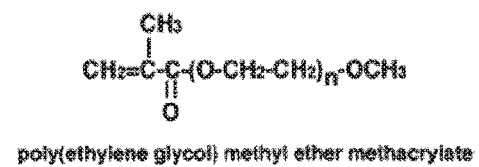
Figure 18A
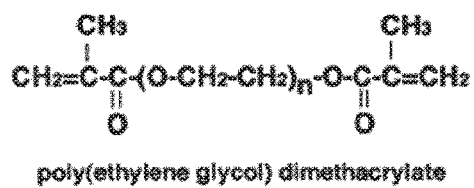
Figure 18B
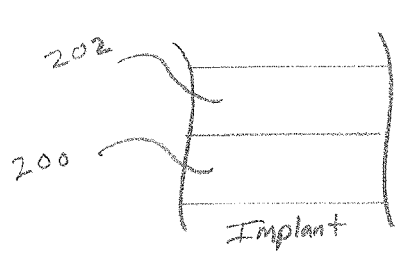
Fig. 19A
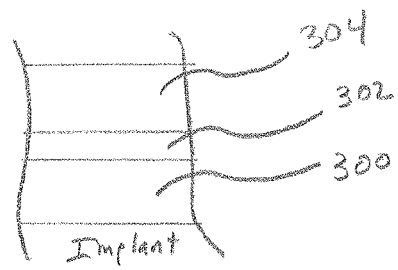
Fig. 19B

COATINGS FOR IMPLANTABLE DEVICES

CROSS REFERENCE TO RELATED APPLICATIONS

This application is a U.S. national phase application, under 35 U.S.C. 371, of PCT/US2019/018764, filed Feb. 20, 2019, which in turn claims priority to U.S. Provisional Application No. 62/632,574, filed Feb. 20, 2018, and U.S. Provisional Application No. 62/634,578, filed Feb. 23, 2018, the disclosures of which are incorporated by reference herein for all purposes.

This disclosure also incorporates the following publications by reference herein for all purposes: WO2017/210316, PCT/US2018/056277 filed Oct. 17, 2018, and PCT/US2018/043753 filed Jul. 25, 2018. For example, any of the coatings herein may be applied to any of the suitable implants described in the patent applications incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Glaucoma is second only to cataract as a leading cause of global blindness and is the leading cause of irreversible visual loss. Worldwide, there were 60.5 million people with open angle glaucoma and angle closure glaucoma in 2010, projected to increase to 79.6 million by 2020, and of these, 74% will have OAG. (Quigley and Broman, in Br J Ophthalmol. 2006; 90(3), pp 262-267). Of those with ACG, it is predicted that 70% will be women and 87% will be Asian. Open-angle glaucoma affects more than 2 million individuals in the United States. Owing to the rapid aging of the US population, this number will increase to more than 3 million by 2020, and approximately a total of 4 million glaucoma cases. Bilateral blindness from glaucoma is projected to affect greater than 11 million by 2020 globally. Risk factors for open-angle glaucoma include increased age, African ethnicity, family history, increased intraocular pressure, myopia, and decreased corneal thickness. Risk factors for angle closure glaucoma include Inuit and Asian ethnicity, hyperopia, female sex, shallow anterior chamber, short axial length, small corneal diameter, steep corneal curvature, shallow limbal chamber depth, and thick, relatively anteriorly positioned lens.

Elevated intraocular pressure ("IOP") is the most important known risk factor for the development of POAG, and its reduction remains the only clearly proven treatment. Several studies have confirmed that reduction of IOP at any point along the spectrum of disease severity reduces progression (Early Manifest Glaucoma Treatment Trial to Advanced Glaucoma Intervention Study). Also, IOP reduction reduces the development of POAG in patients with ocular hypertension (OHT) and reduces progression in patients with glaucoma despite normal IOP, as seen in the Collaborative Normal Tension Glaucoma Study. The normal IOP for 95% of Caucasians is within the range of 10-21 mm Hg. While increased IOP is a strong risk factor for the development of glaucoma, it must be remembered that many people with glaucoma have untreated IOPs of 21 mm Hg or less. In general, it is estimated that approximately 50% of POAG is of the normal tension variety. However, studies have found a wide range in the prevalence of normal tension glaucoma among individuals with OAG. For example, normal tension glaucoma was diagnosed in ⅓ of the OAG patients in the Barbados Eye Studies, and 85% of the individuals with OAG in a Chinese population. At this time, the risk associated with long-term fluctuation of IOP over months to years remains controversial. The EGPS and Early Manifest Glaucoma Treatment Trial found that long-term IOP fluctuations were not associated with progression of glaucoma, while the AGIS study found an increased risk of glaucoma progression with increased long-term IOP fluctuation, especially in patients with low IOP.

Currently, IOP reduction remains the only treatment option for glaucoma, with options depending on many factors such as the type of glaucoma. Current monitoring of IOP occurs in the offices of a vision care practitioner, typically an ophthalmologist, ranging from once a year to once every 3-6 months, once glaucoma is diagnosed. It is known that IOP varies over a wide range in individuals, including a diurnal fluctuation, longer term variations and occurrence of spikes in IOP, therefore a single measurement cannot provide adequate data to diagnose an elevated IOP, requiring prescription of pressure regulating or pressure reducing medication. Treatment options for reduction of IOP include medical therapy, such as beta blockers, alpha agonists, miotics, carbonic anhydrase inhibitors, and prostaglandin analogues, administered as eyedrops, up to 4 times a day; laser treatment, such as argon laser trabeculoplasty (ALT), selective laser trabeculoplasty (SLT), neodymium-doped yttrium aluminum garnet (Nd:YAG) laser iridotomy, diode laser cycloablation, and laser iridoplasty; surgical procedures including iris procedures (e.g., peripheral iridectomy), angle procedures (e.g., goniotomy and trabeculotomy), filtration procedures (e.g., trabeculectomy) and non-penetrating filtration procedures (e.g., deep sclerectomy and viscocanalostomy); and drainage shunts including episcleral implants (e.g., Molteno, Baerveldt, and Ahmed) or mini-shunts (e.g., ExPress Mini Shunt and iStent).

Prevalence of glaucoma in white (A) and black and Hispanic (B) subjects is shown in BES, Baltimore Eye Survey, Baltimore, Md.; BDES, Beaver Dam Eye Study, Beaver Dam, Wis.; BMES, Blue Mountain Eye Study, Sydney, NSW; Melbourne VIP, Melbourne Visual Impairment Project, Melbourne, VIC; RS, Rotterdam Study, Rotterdam, the Netherlands; Barbados, Barbados Eye Study, Barbados, West Indies; KEP, Kongwa Eye Project, Tanzania; and Proyecto VER, Vision Evaluation Research, Nogales and Tucson, Ariz. "Eye Diseases Prevalence Research Group (2004) Prevalence of open-angle glaucoma among adults in the United States.", *Arch Ophthamol* 122: 532-538.

A substantial majority of glaucoma patients are treated by medication to control IOP, sometimes over three decades. Patients treated surgically or using laser treatment may also be administered medication. Lack of compliance of patients to long term medication protocols is exacerbated by advancing age and lack of positive concrete immediate incentives.

Monitoring compliance—continuous monitoring of IOP replaces the standard practice of monitoring IOP episodically, hence provides a more accurate and detailed account of patient compliance, enabling the caregiver to take steps to take additional steps to enhance compliance if required.

Monitoring efficacy of prescribed treatment—continuous IOP data following a change in treatment modality or protocol provides the caregiver with a prompt feedback on the efficacy of the change in treatment and thereby supports a better outcome.

Post market monitoring of approved glaucoma treatments—newly approved glaucoma treatments may require post market monitoring by health care agencies in order to monitor safety and efficacy on the targeted patient population. Data from continuous monitoring of IOP may be submitted by manufacturers of newly approved drugs or devices to meet this requirement.

Clinical research on efficacy of novel glaucoma treatments—data recorded may be used by clinical researchers to monitor efficacy and may be submitted to regulatory authorities for prompt approval, if the results so warrant.

The references below describe some earlier concepts related to monitoring intraocular pressure.

1. "An implantable microfluidic device for self-monitoring of intraocular pressure", by Mandel, Quake, Su and Araci, in *Nature Medicine* 20, 1074-1078 (2014). Three images of a microfluidic intraocular sensor are shown in this reference. The sensor comprises a 50×50 µm$^2$ cross-section channel connected to the eye fluid on one side and to a 0.5 mm×2.0 mm×0.3 mm volume reservoir ($V_{reservoir}$) on the other.

2. "Implantable parylene-based wireless intraocular pressure sensor", by Chen, Rodger, Saati, Humayun and Tai in IEEE 21$^{st}$ International Conference on Micro Electro Mechanical Systems, 2008. MEMS 2008. This paper presents an implantable, wireless, passive pressure sensor for ophthalmic applications. Two sensor designs incorporating surface-micro-machined variable capacitor and variable capacitor/inductor are implemented to realize the pressure sensitive components. The sensor is monolithically microfabricated using parylene as a biocompatible structural material in a suitable form factor for increased ease of intraocular implantation. Pressure responses of the microsensor are characterized on-chip to demonstrate its high pressure sensitivity (>7000 ppm/mmHg) with mmHg level resolution. An in vivo animal study verifies the biostability of the sensor implant in the intraocular environment after more than 150 days.

3. "Rollable and implantable intraocular pressure sensor for the continuous adaptive management of glaucoma", Piffaretti, Barrettino, Orsatti, Leoni, Stegmaier, in Conference Proceedings IEEE Eng Med Biol Soc, 2013; 2013: 3198-201. doi: 10.1109/EMBC.2013.6610221.

4. "Implantable microsensor, telemetrically powered and read out by patient hand-held device", by Implandata Ophthalmic Products GmbH Kokenstrasse 5 30159 Hannover Germany, 2014. The Eyemate® by Implandata Ophthalmic Products GmbH is also an example.

5. "Preliminary study on implantable inductive-type sensor for continuous monitoring of intraocular pressure", by Kim Y W, Kim M J, Park, Jeoung, Kim S H, Jang, Lee, Kim J H, Lee, and Kang in *Clinical & Experimental Ophthalmology*, 43(9), pp 830-837, 2015.

6. "An intra-ocular pressure sensor based on a glass reflow process", by Haque and Wise in *Solid-State Sensors, Actuators, and Microsystems Workshop, Hilton Head Island*, S.C., Jun. 6-10, 2010.

7. Some earlier approaches used a capacitive-based membrane pressure sensor. For example, a diaphragm can deflect under pressure, changing the effective distance between two parallel plates, and thus increasing the measured capacitance across the plates. An example is "Miniaturized implantable pressure and oxygen sensors based on polydimethylsiloxane thin films", Koley, Liu, Nomani, Yim, Wen, Hsia: in *Mater. Sci. Eng. C* 2009, 29, 685-690.

8. "Microfabricated implantable Parylene-based wireless passive intraocular pressure sensors", by Chen, Rodger, Saati, Humayun, Tai: *J. Microelectromech. Syst.* 2008, 17, 1342-1351.

9. "An Implantable, All-Optical Sensor for Intraocular Pressure Monitoring", by Hastings, Deokule, Britt and Brockman in Investigative *Ophthalmology & Visual Science*, 2012. Vol. 53, pp 5039. A simplified approach to IOP monitoring based on a near infrared (NIR) image of an implanted micromechanical sensor is presented. The sensor chip contains one or more vacuum reference cavities formed by a flexible membrane, a rigid substrate, and a thin spacer. Both substrate and membrane partially reflect light to form an interference pattern of concentric rings. These rings shift radially as the membrane deflects in response to pressure changes. IOP is measured by analyzing a narrow-band NIR image of the pattern.

10. "Chronically Implanted Pressure Sensors: Challenges and State of the Field", A Review by Yu, Kim and Meng, in *Sensors* 2014, 14, 20620-20644; doi:10.3390/s141120620.

12. "Polymer-based miniature flexible capacitive pressure sensor for intraocular pressure (TOP) monitoring inside a mouse eye", by Ha, de Vries, John, Irazoqui, and Chappell in *Biomed Microdevices* (2012) 14:207-215, DOI 10.1007/s10544-011-9598-3.

13. "Intra-ocular pressure sensor", U.S. Pat. No. 8,475,374 B2, by Irazoqui, Chow, Chappelle, Yang, and Ziaie, 2013.

SUMMARY OF THE DISCLOSURE

The disclosure is related to coatings for implantable devices. While in some embodiments the coatings are disposed on intraocular lenses, the coatings herein may be applied to a variety of other implantable devices as well, such as intraocular pressure sensors.

An aspect of the disclosure is an implantable device with a biocompatible coating, the device comprising an implantable device having an outer surface and a coating disposed on the outer surface of the implantable device. The coating can include an inner layer disposed on the implantable device outer surface, and an exterior layer exposed to the ambient environment. The inner layer can have an inner cross link density and the exterior layer can have an exterior cross link density that is lower than an inner layer cross link density.

The exterior layer may have an exterior refractive index and the inner layer may have an inner refractive index different than the exterior refractive index. The exterior refractive index can be less than the inner refractive index. The exterior refractive index may be between 1.39 and 1.44. The inner refractive index may be between 1.44 and 1.50.

At least one of the outer layer and the inner layer can have a gradient refractive index, with the refractive index being greater at an innermost location of the layer than at an outermost location of the layer.

The exterior layer can have a water content that is higher than an inner layer water content.

The inner layer may include at least one agent that is adapted to be released from the inner layer. An agent may inhibit the expression of a cytokine (e.g., TGF-β) in order to minimize the adhesion of macrophages. An agent may be Pirfenidone. An agent may be a COX-1 or COX-2 inhibitor. An agent may be an anticlotting agent. An agent may be a fibrin inhibitor. The coating can have a molecular structure adapted to release the at least one agent over a period not less than 1 week and not more than 25 weeks. The coating may further include a diffusion regulatory mechanism. The coating may further comprise an intermediate layer between the inner layer and the exterior layer, and wherein the intermediate layer can have a structure that comprises the diffusion regulatory mechanism. An agent can be a steroid, such as dexamethasone and/or prednisolone.

The coating can be preloaded with at least one of an inhibitor and regulator of the cytokine TGF β, a steroid, an anti-inflammatory agent, an anticlotting agent, and a Cox 1 and Cox 2 inhibitor for sustained release into tissue subsequent to implantation, or any combination thereof.

The inner and exterior layers can have different area densities of hydroxyl groups.

The implant can further comprise an intermediate layer between the inner layer and the exterior layer. An intermediate cross link density can be different than the inner cross link density and the exterior cross link density. The inner layer, intermediate layer, and exterior layer can have different area densities of hydroxyl groups. Each of the inner, intermediate, and exterior layers may comprise a unique polyethylene glycol based cross-linked network of different cross-link density and crystallinity. The intermediate layer can have a thickness that is less than an inner layer thickness and an exterior layer thickness. A thickness of the entire coating can be from 50 to 200 microns, and optionally wherein each layer has an individual thickness from 10 microns to 50 microns.

The inner layer and exterior layer can comprise polyethylene glycol based cross-linked networks.

The exterior layer can be hydrophilic and can have at least one hydroxyl group per molecule.

The exterior layer can comprise a hydrophilic monomer, wherein the hydrophilic monomer is monofunctional, difunctional, trifunctional or tetrafunctional in polymerization reactivity.

The coating can adsorb water upon hydration, optionally within a range from 35-75% by weight of water upon equilibration.

The coating can have a glass transition temperature in the range of −20 C to +10 C in a dehydrated state.

The coating can have an elongation to break in a range of 30% to 250%.

The coating can have a tensile modulus in the range of 0.01 to 5.0 MP.

The implantable device can further comprise any combination of features herein, including methods of manufacture.

An aspect of the disclosure is a method of creating a biocompatible coating on at least a portion of an intraocular lens, whether or not the intraocular lens is in a fully manufactured state, wherein the coating is any of the coatings herein.

An aspect of the disclosure is an implantable device with a biocompatible coating, comprising an implantable device having an outer surface, and a coating disposed on the outer surface of the implantable device. The coating can include an inner layer disposed on the implantable device outer surface, and an exterior layer exposed to the ambient environment. The inner layer and the exterior layer can each comprise pendant hydroxyl groups, wherein a number density of hydroxyl groups is lower in the inner layer than in the exterior layer.

The inner layer can comprise at least one agent that is adapted to be released from the inner layer. An agent can inhibit the expression of a cytokine (e.g., TGF-β) in order to minimize the adhesion of macrophages. An agent can be Pirfenidone. An agent can be a COX-1 or COX-2 inhibitor. An agent can be an anticlotting agent. An agent can be a fibrin inhibitor. The coating may have a molecular structure adapted to release the at least one agent over a period not less than 1 week and not more than 25 weeks. The coating may further comprises a diffusion regulatory mechanism. The coating may further comprise an intermediate layer between the inner layer and the exterior layer, and wherein the intermediate layer optionally has a structure that comprises the diffusion regulatory mechanism. An agent may be a steroid, such as dexamethasone and/or prednisolone.

The coating can be preloaded with at least one of an inhibitor and regulator of the cytokine TGF β, a steroid, an anti-inflammatory agent, an anticlotting agent, and a Cox 1 and Cox 2 inhibitor for sustained release into tissue subsequent to implantation, or any combination thereof.

The implantable device can further comprise an intermediate layer between the inner layer and the exterior layer. An intermediate cross link density can be different than the inner cross link density and the exterior cross link density. The inner layer, intermediate layer, and exterior layer can have different area densities of hydroxyl groups. Each of the inner, intermediate, and exterior layers comprise a unique polyethylene glycol based cross-linked network of different cross-link density and crystallinity. The intermediate layer can have a thickness that is less than an inner layer thickness and an exterior layer thickness. The thickness of the entire coating may be from 50 to 200 microns, and optionally wherein each layer has an individual thickness from 10 microns to 50 microns.

The inner layer and the exterior layer may comprise a polyethylene glycol based cross-linked networks.

The exterior layer may be hydrophilic and optionally has at least one hydroxyl group per molecule.

The exterior layer may comprise a hydrophilic monomer, wherein the hydrophilic monomer is monofunctional, difunctional, trifunctional or tetrafunctional in polymerization reactivity.

The coating may adsorb water upon hydration, optionally within a range from 35-75% by weight of water upon equilibration.

The coating may have a glass transition temperature in the range of −20 C to +10 C in a dehydrated state.

The coating may have an elongation to break in a range of 30% to 250%.

The coating may have a tensile modulus in the range of 0.01 to 5.0 MP.

The coating may include any other feature described herein.

An aspect of the disclosure is a method of creating a biocompatible coating on at least a portion of an intraocular lens, whether or not the intraocular lens is in a fully manufactured state, wherein the coating may be any of the coatings herein.

In any of the coatings herein, at least one of an inner layer and an exterior layer includes medicaments, at least two of which are an antibiotic, a non-steroidal anti-inflammatory agent, a steroid, an anticlotting agent and an agent that inhibits fibrosis.

BRIEF DESCRIPTION OF THE DRAWINGS

FIGS. 4A, 4B and 4C illustrates some exemplary views of an exemplary implant, which can be the same as or similar to the exemplary implant FIG. 2.

FIGS. 12A-12G illustrate an exemplary implant that has a general square configuration.

FIG. 17 shows the molecular structure of Prednisolone.

FIGS. 18A and 18B illustrate exemplary mono and dimethacrylate derivatives of PEG oligomers, respectively, that may be incorporated into one or more layers of any of the multilayered coatings herein.

FIG. 19A illustrates an exemplary coating on an implant, the coating including first and second layers.

FIG. 19B illustrates an exemplary coating on an implant, the coating including first, second, and third layers.

DETAILED DESCRIPTION

Figure 1:
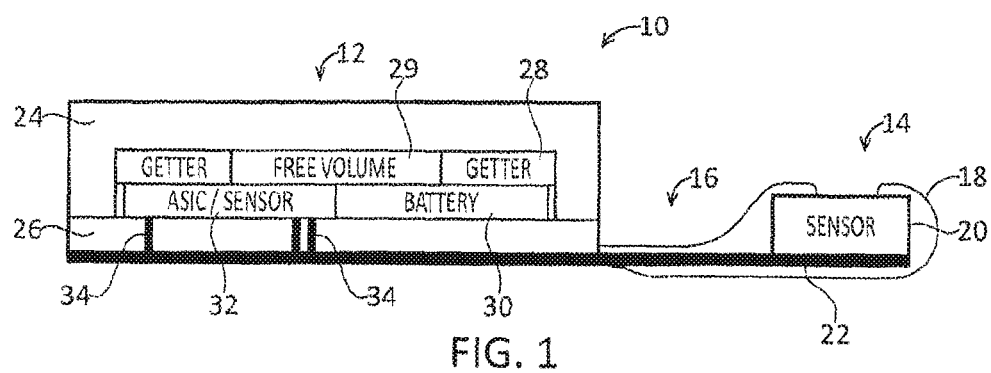
FIG. 1 schematically illustrates exemplary components of an exemplary implant.

This disclosure relates generally to coatings on implantable devices, including methods of manufacture. In some exemplary embodiments the coatings can be applied to a variety of implantable devices in general, such as intraocular pressure ("IOP") sensors. In some particular examples the coatings are applied to intraocular lenses.

Some aspects of this disclosure relate generally to intraocular pressure sensors, intraocular pressure sensing, and systems for using, and the use of, the sensed pressure or information indicative of the sensed pressure. Much of the disclosure herein related to IOP sensors is also described in WO2017/210316, the full disclosure of which is incorporated by reference for all purposes. The sensors and methods herein may also, however, be used in sensing pressure in areas near or outside of the eye. For example, sensors and methods of use herein may be used in episcleral, cardiac or neural applications, including the brain.

Some aspects of the disclosure include implantable intraocular pressure sensors that are adapted, configured, and sized to be positioned and stabilized within the eye and communicate, optionally wirelessly, with one or more devices positioned within or outside the eye. A wireless intraocular pressure sensor may be referred to herein as a "WIPS," and an implantable device may be referred to herein an implant, or an implantable portion of a system.

Some of the devices, systems, and methods of use herein provide an exemplary advantage that they can sense intraocular pressure more frequently than possible with traditional tonometry and office visits, and can thus provide more frequent information regarding the change in pressure of an eye. For example, some devices herein are adapted to sense intraocular pressure continuously, substantially continuously, or periodically (regular intervals or non-regular intervals) when implanted in an eye.

An autonomous, implantable sensor is preferred in order to provide monitoring, optionally continuous, of IOP, in order to avoid relying on the patient to perform monitoring and management tasks that can be quite onerous for a sensor continuously recording IOP data. An autonomous implanted sensor can include an electrically operated sensor that measures pressure of the aqueous humor and converts it to an electrical signal, an internal power source, optionally provided by a rechargeable battery, an electrical controller such as a microcontroller or an ASIC to manage the electronic system, a memory unit comprising volatile and/or non-volatile memory, and a wireless link in order to, optionally, receive power wirelessly, download data to an external device, and optionally a data uplink to allow reprogramming capability. The data can be downloaded into a smart phone or a tablet that serves a data uplink to a caregiver's computer via a wireless or cabled network. Power can be provided from an external charging unit that has its own power management integrated circuit (PMIC), and may also have a wireless data transfer capability, and thus can function as an interface between the implanted device and the smart phone or a tablet.

FIGS. 1-14 illustrate aspects of merely exemplary implantable devices that can be used with the systems and methods of use herein. FIG. 1 schematically illustrates exemplary components of an exemplary implant 10. Any of the implants herein can include a pressure sensor, a housing that hermetically surrounds an ASIC and battery, and a flexible substrate/connector to which the housing and pressure sensor are secured. The flexible substrate/connector can include an electrical connection to the pressure sensor and antenna.

One of the challenges when designing a wireless implant that includes an intraocular pressure sensor is conceiving of a way to incorporate components into a hermetically sealed device that includes a pressure sensor, antenna, power source, and controller, wherein the device can be implanted securely and safely into the eye, and still provide and communicate sensed data or information indicative of intraocular pressure to an external device.

Exemplary implant 10 includes first portion 12 secured to sensor portion 14 via connector portion 16. Substrate 22 extends between sensor portion 14 and first portion 12. Sensor portion 14 includes at least one pressure sensor 20 disposed within an encapsulation 18, optionally silicone or other similar material. Sensor 20 is in operable pressure communication with the external environment, such that external pressures can be transmitted to pressure sensor 20. This can be, for example, via an area of sensor portion 14 (e.g., encapsulation 18) that does not extend over the pressure sensor 18 as shown.

Substrate 22 carries electronics that allow signals from sensor 18 to be communicated to first portion 12. Data or signals indicative of sensed data can be communicated via sensor portion 14 to controller 32 with sealed vias 32 and 34, which is this exemplary embodiment comprises an ASIC. First portion 12 includes top casing 24 and bottom casing 26, which together form a hermetic seal that houses components therein. Top and bottom casings can be, in some embodiments, rigid glass material or titanium. The first portion also includes battery 30, and can also include water getter 28, and free volume 29.

Figure 2:
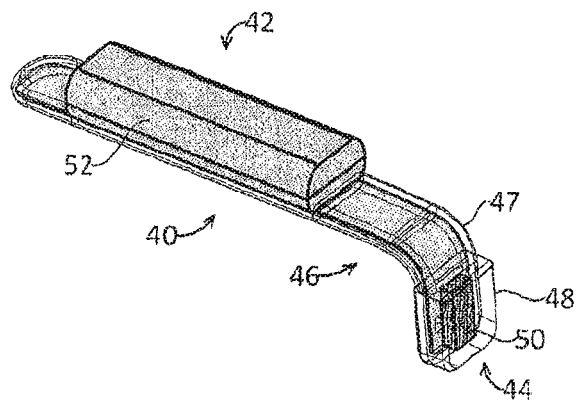
FIG. 2 illustrate an exemplary implant with a flexible connector portion.
Figure 3:
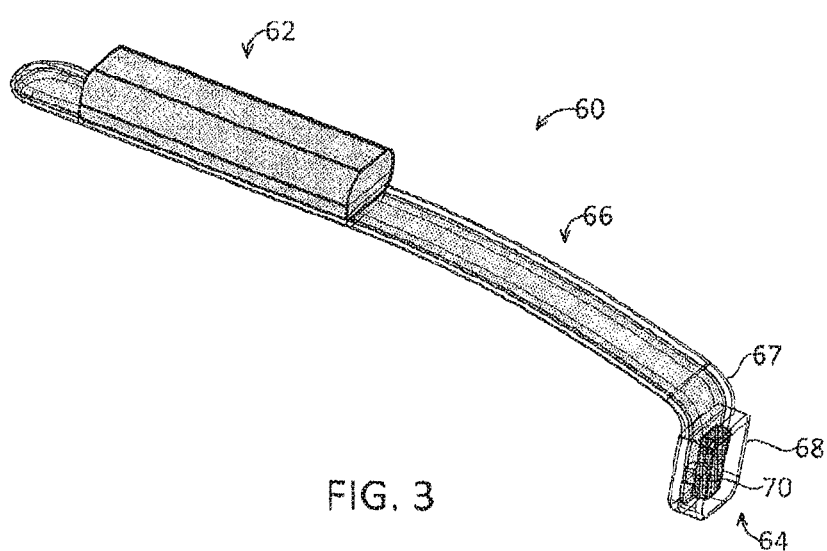
FIG. 3 illustrate an exemplary implant with a longer flexible connector portion than the exemplary implant in FIG. 2.

FIGS. 2 and 3 illustrate substantially the same implants 40 and 60, with implant 60 having a longer flexible connector portion 66 than implant 42's connector portion 46. Both implants include a first portion 42/62, respectively, secured to the sensor portion via the flexible connector portion. Both implants also include sensor portion 44 and 64 respectively, which include sensors 50 and 70, respectively. First portions 42 and 62 can include any of the components of the implants herein, such as a power source, controller (e.g., ASIC), memory, water getter, etc.

Connector portions 46 and 66 each also include bend regions 47/67, respectively. Bend regions 47 and 67 are closer to sensor portions 44/64 than first portions 42/62. The bend regions are optional, as other embodiments do not necessarily need to include them.

In some embodiments the implant has an overall length such that the pressure sensor can be positioned in the anterior chamber and the housing is positioned in the suprachoroidal space of an average adult. The flexible substrate can include a bend, or region of increased curvature, as shown in some embodiments herein.

FIGS. 4A-4C illustrates some exemplary views of the exemplary implant, which can be the same or similar as implant 40 from FIG. 2, and which illustrate exemplary specific dimensions. The implants herein can be configured and sized to fit within a 0.6 mm to 2.0 mm outer diameter, and in particular a 1.0 mm outer diameter lumen, such as a needle. The dimensions shown in the FIGS. 4A-4C are illustrative and not limiting.

Implant 80 includes first portion 82, sensor portion 84, and connector portion 86. A casing or encapsulation 88 extends around sensor portion 84, connector portion 86, and along the bottom of first portion 82. Sensor portion 84 includes pressure sensor 90 disposed within encapsulation 88, but encapsulation can have a window therein so sensor 90 is in pressure communication with the environment. The first portion 82 can include any of the electronics and other components (battery, memory, antenna, etc.) described herein. Substrate or base layer 92 extends from the sensor portion 84 to the first portion 82, and carries electronics (e.g., flex circuits printed on a substrate) that electrically couple sensor 90 and electronics within first portion 82. Substrate 92 also comprises an antenna adapted for wireless data and power transfer.

As shown in the side view of FIG. 4A, the exemplary length of the housing of first portion 82 is 3.3 mm, whereas the height of the housing and encapsulation is 0.81 mm. As shown in the top view of FIG. 4B, the overall length of the implant is 6.0 mm. As shown in the front view of FIG. 4C, the overall width is 1.0 mm, while the exemplary sensor portion (including encapsulation) is 0.9 mm wide and 1.2 mm tall. The height of the overall device 3.0 mm.

FIG. 4A illustrate that connector portion 86 has a bend 83 along its length closer to the sensor portion 84 than first portion 82, and is flexible along its length, and the flexibility of connector portion 86 allows sensing portion 84 to move relative to first portion 82. In an at-rest, or nondeformed configuration, the bend 83 in connector portion 86 is such that connector portion 86 and sensor portion 84 have axes that are orthogonal to each other. Bend 83 can have a single radius of curvature of can have a varying radius of curvature.

Encapsulation 83 can be a deformable material such as silicone (compatible with off-the-shelf piezo and capacitive MEMS sensors). Top and bottom portions 94 and 96 can be glass or titanium, as is set forth herein.

The flexible electronics on the substrate can include the contacts for the sensor and the antenna. Incorporating an antenna into the flexible substrate is one way of incorporating an antenna into a compact implantable device while still allowing for data and power transmission.

Figure 5A:
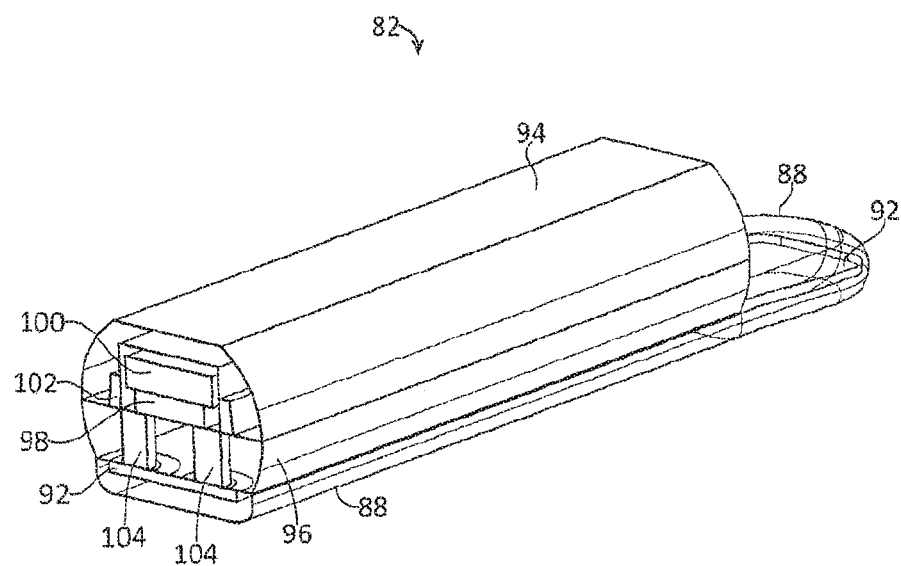
FIGS. 5A and 5B illustrate perspective sectional and front sectional views, respectively, of an exemplary first portion of an implant.
Figure 5B:
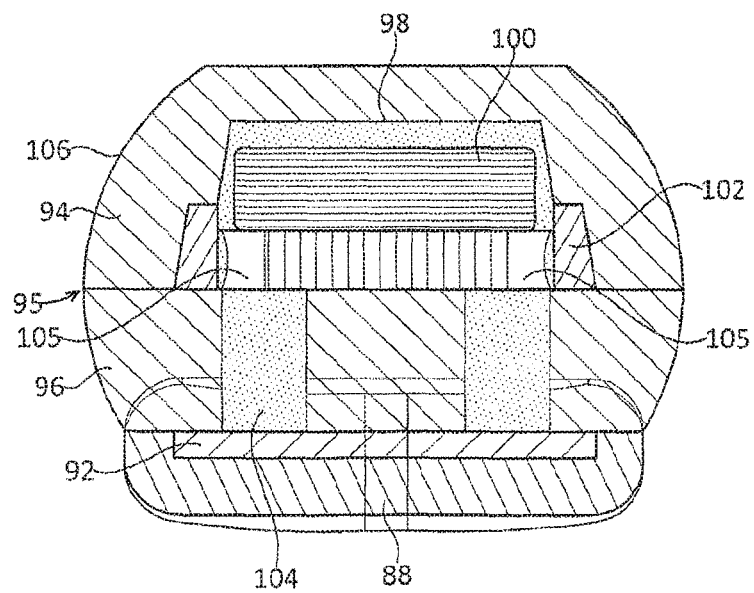

FIGS. 5A and 5B illustrate perspective sectional and front sectional views, respectively, of first portion 82. First portion 82 includes top and bottom housings 94 and 96, respectively, that interface at hermetic seal 95. The flexible electronics on substrate 92 are in electrical communication with vias 104, which are electrically coupled to housing electronics such as processor 98 (which can be an ASIC) and rechargeable battery 100. Optional water getter 102 is also disposed in the top portion of first portion 82.

First portion 82 also includes coating 106 thereon, which can be, for example without limitation, gold.

Figure 6A:
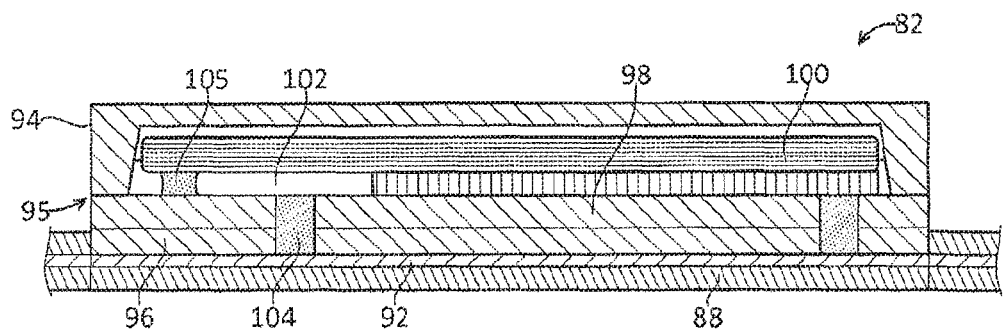
FIGS. 6A and 6B show side assembled and side exploded view of the exemplary first portion of an implanted device from FIGS. 5A and 5B.
Figure 6B:
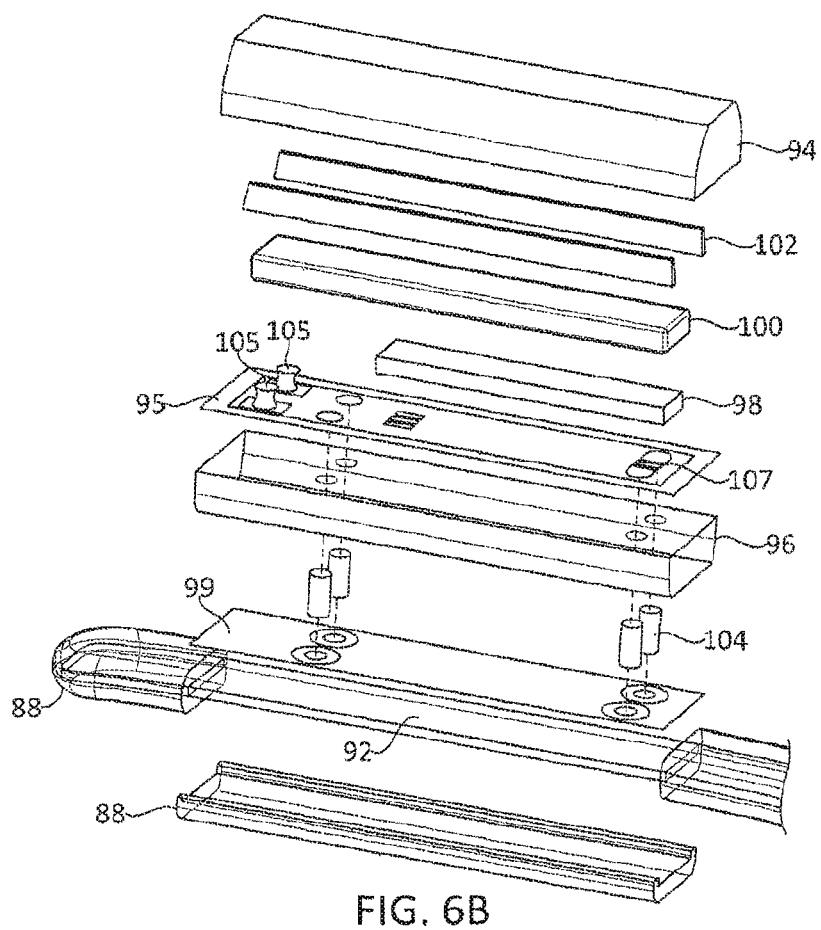

FIGS. 6A and 6B show side assembled and side exploded view of first portion 82 of an implanted device from FIGS. 5A and 5B. This first portion can be incorporated into any of the other embodiments herein. The relevant description of FIGS. 5A and 5B can similarly apply to FIGS. 6A and 6B. FIG. 6B illustrates more clearly the assembly and the manner in which the components are electrically coupled. The housing includes metallization 99, which provides an electrical connection with the flexible electronics on the substrate 92. Disposed between top housing 94 and bottom housing 96 is seal 95 and electrical connections 107, which are electrically coupled to vias 104. Connects 105 are in electrical communication with battery 100.

Figure 7A:
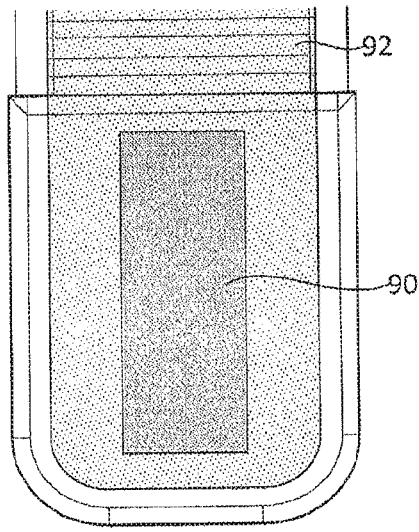
FIGS. 7A, 7B and 7C illustrate an exemplary sensor portion of an implant.
Figure 7B:
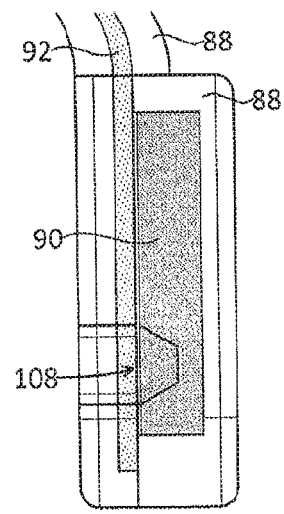
Figure 7C:
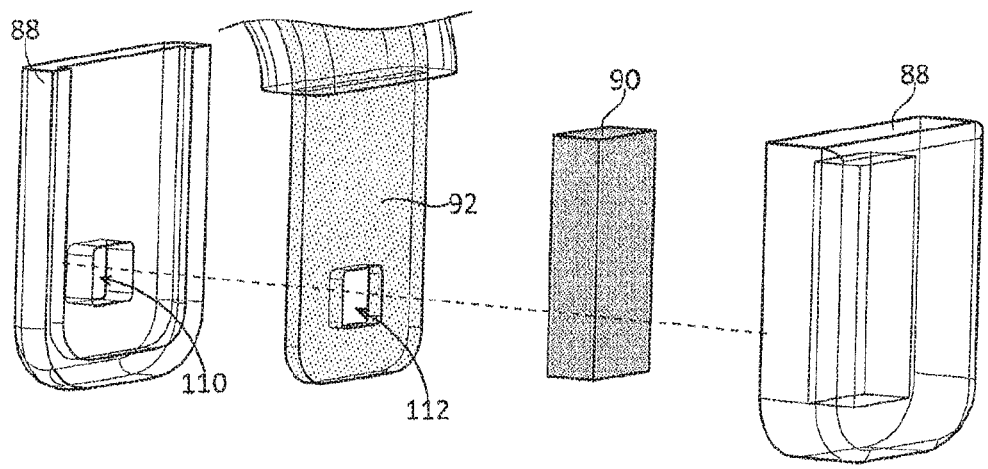

FIGS. 7A, 7B and 7C illustrate exemplary sensor portion 84 from FIGS. 4A-4C, but can be any of the sensor portions herein. FIG. 7A is a front view, FIG. 7B is a side view, and FIG. 7C is an exploded perspective front view. What can be seen is that encapsulation 88 and substrate 92 both include aligned windows or apertures therein, which allows the pressure sensor to communicate with the external environment. The windows together create opening 108 (see FIG. 12B) in the sensor portion. The windows may be filled with a material that allows pressure to be communicated to pressure sensor. The pressure sensor is "face down" on the flexible substrate and thus able to sense pressure via the access holes shown. The sensor electrical contact pads can be directly in contact with electronics on the flexible substrate, which can remove the need for wiring/wire bonding and requires an opening in the flex substrate and an opening in the encapsulation. Conductive lines/bond pads, and optional Parylene C coatings at piezo bridges are not shown in the figures, but can be included.

In any of the delivery procedures herein, an incision made in the eye during delivery can be 1 mm oval, or may be 1.2 mm.

FIGS. 8A-8E illustrate an exemplary embodiment of implant 140 and exemplary delivery device. In this exemplary embodiment, the implant does not include a flexible elongate connector portion with a bend as in some of the embodiments above.

FIG. 8A shows a portion of implant 140. Sensor 142 is disposed at a first end of implant 140, and is coupled to housing 144. Housing 144 can include any components of any of the first portions herein. Housing 144 includes the encapsulation that encapsulates antenna 152, controller 150 (e.g., an ASIC), power source 146, and feedthrough 148 that connects ASIC 150 to the antenna 152. As in other embodiments herein, implant 140 can also include a metallic coating on the glass housing for hermeticity, one or more electrical lines on one or more glass or titanium substrates, an antenna ground plane, and a water getter (inside housing).

FIGS. 8Bi and 8Bii illustrate implant 140 from FIG. 4A but includes a biocompatible cover 160, optionally a polymeric material, including a plurality of sensor protective flaps 162 that extend at a first end (two are shown), a mechanical stop 164 for interfacing with a delivery device for insertion, and a conical second end 166 to ease the injection. Implant 140 is disposed inside cover 160, with two sides of sensor 140 protected by the flaps 162. Top and bottom sides of sensor 142 are not covered by cover 160.

Figure 8C:
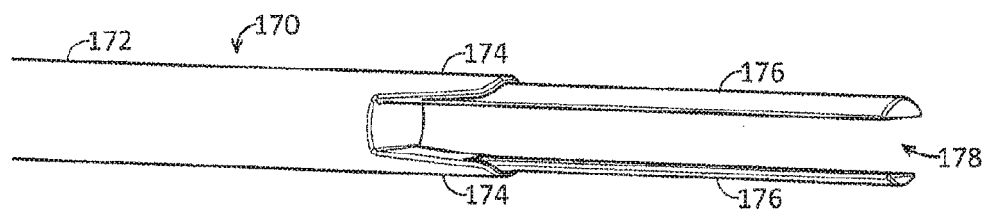
FIGS. 8A, 8Bi, 8Bii, 8C, 8D and 8E illustrate an exemplary embodiment of an implant and an exemplary delivery device.
Figure 8D:
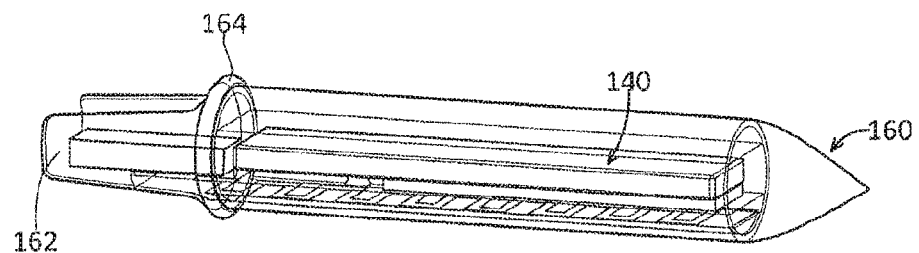
Figure 8E:
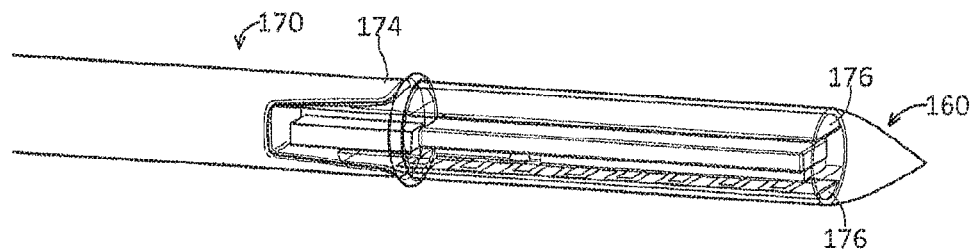

FIGS. 8C and 8E illustrates an exemplary delivery tool 170 adapted and configured to interface with cover 160 (with implant 140 therein), which is shown in FIG. 8D, but inverted relative to FIG. 8Bi. Delivery tool 170 is adapted to facilitate the implantation of implant 140 and cover 160. Delivery tool 170 includes a main body 172 from which extend a first plurality of extensions 174 and a second plurality of extensions 176 (in this embodiment there are two of each). Extensions 174 are shorter than extensions 176 and are radially outward relative to extensions 176. One of the extensions 174 is aligned with one of the extensions 176, and the other of extensions 174 is aligned with the other of extensions 176. The plurality of extensions 174 interface with stops 164 of cover 160 when cover 160 is fully advanced within the inner space 178 of tool 170. Arms or extensions 162 on cover 160 are similarly sized and configured to fit within the space defined by arms 174. The radially inner arms 176 are positioned just slightly radially inward, and are sized and configured to be disposed within elongate channels within cover 160, which can be seen in FIG. 8E. In this embodiment body portion 172 of tool 170 has the same or substantially the same outer diameter as the cover 160. The elongate arms 176 can stabilize the relative positions of tool 170 and the implant during the delivery process.

Figure 9A:
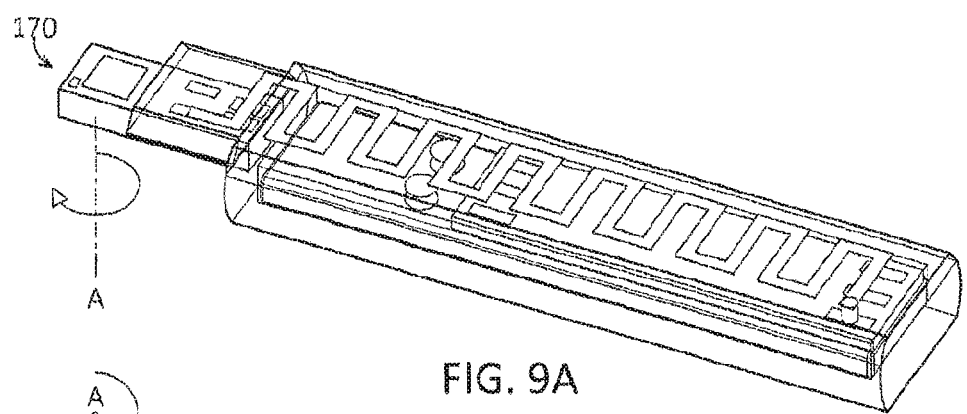
FIGS. 9A, 9B and 9C illustrate an exemplary implant, wherein the implant is adapted such that the sensor can rotate relative to the main housing about an axis, and the rotation axis is perpendicular relative to the main implant body.
Figure 9B:
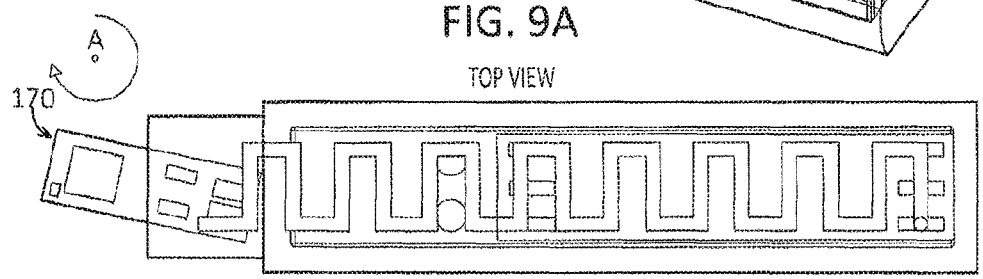
Figure 9C:
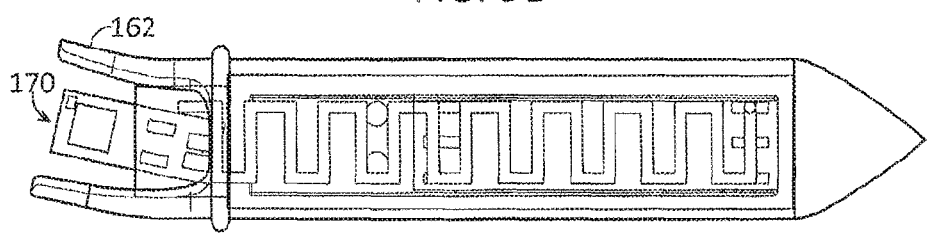

FIGS. 9A-9C illustrate an exemplary alternative embodiment to that shown in FIGS. 8A and 8B, but in this embodiment the implant is adapted such that sensor 170 can rotate relative to the main housing about axis "A," and the rotation axis is perpendicular relative to the main implant body. All other components are described above and are not relabeled for clarity. FIG. 9A is a perspective view, and FIG. 9B is a top view. FIG. 9C is a top with cover, showing the two arms flexing with the rotation of the sensor. The protective cover follows the sensor orientation, as shown in FIG. 9C. In some embodiments the sensor can rotate up to 90 degrees, and in some embodiments no more than 45 degrees, such as 40 degrees or less, or 35 degrees or less, or 30 degrees or less, or 25 degrees or less, or 20 degrees or less, such as 12 degrees. In some embodiments the sensor is rotatable from 0 to about 90 degrees (e.g., 95 degrees). The implant in FIGS. 9A-C can be the same as the implant in FIGS. 8A-E in all other regards.

Figure 9D:
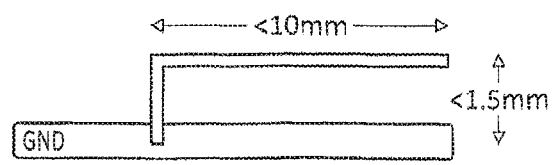
FIGS. 9D and 9E illustrate merely exemplary antenna design and placement in any of the implants herein.
Figure 9E:
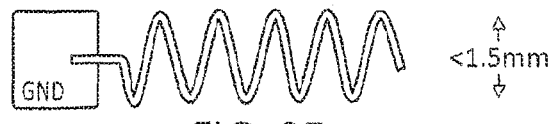

FIGS. 9D and 9E illustrate merely exemplary antenna design and placement in any of the implants herein. The antennas in the implant in FIG. 9A-9C can have other configurations and sizes as well.

Exemplary lengths for the implants shown in FIGS. 8A and 8A (without the cover) are 3-5 mm, such as 3.3 mm to 4.7 mm, such as 3.5 mm to 4.5 mm, such as 3.7 mm to 4.3 mm, such as 4 mm. Exemplary lengths for the covers herein, such as cover 160 from FIG. 8Bi are 4 mm to 6 mm, such as 4.3 mm to 5.7 mm, such as 4.5 mm to 5.5 mm, such as 4.7 mm to 5.3 mm, such as 5 mm. Exemplary widths for the implants shown in FIGS. 8A and 8A (without the cover) are 0.5 mm to 1.5 mm, such as 0.7 mm to 1.3 mm, such as 1 mm.

Figure 10A:
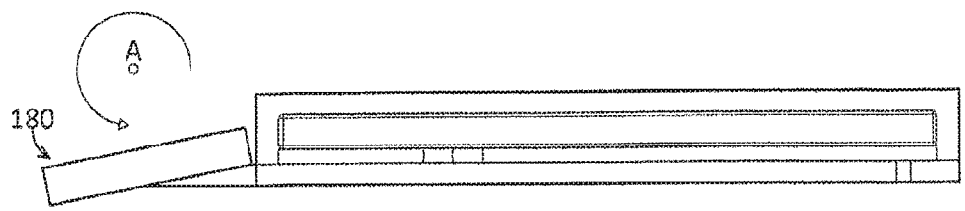
FIGS. 10A and 10B (side and top views, respectively) illustrate an exemplary implant that is adapted such that the sensor can rotate relative to the main housing about an axis, such that is can flex up or down relative to the elongate axis of the main housing.
Figure 10B:
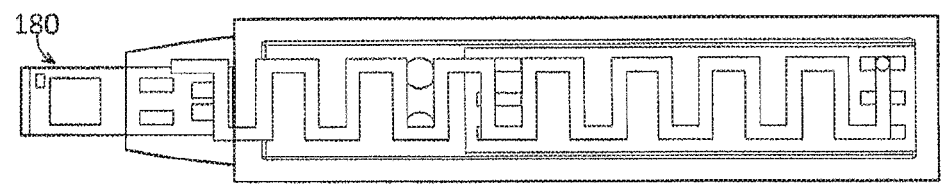

FIGS. 10A and 10B (side and top views, respectively) illustrate an alternative implant similar to that shown in FIGS. 9A-C, but in this embodiment the implant is adapted such that sensor 180 can rotate relative to the main housing about axis "A," such that is can flex up or down relative to the elongate axis of the main housing. This embodiment may benefit from an angled sensor contact plane in the substrate.

Figure 11A:
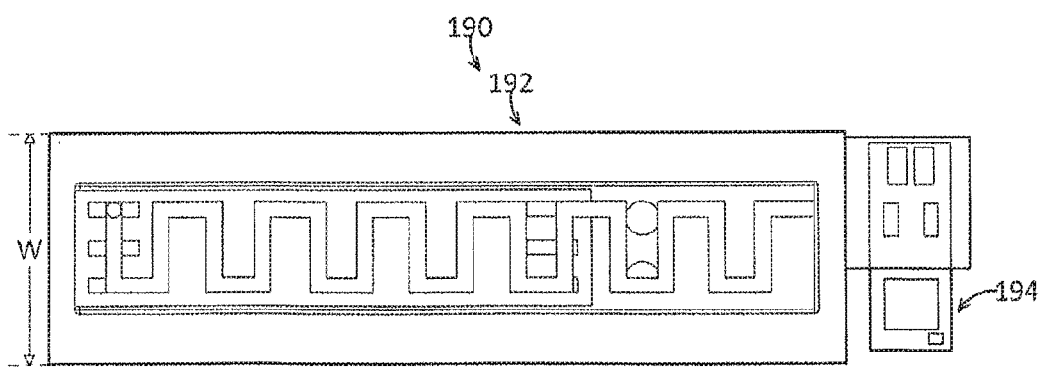
FIGS. 11A and 11B (top and side views, respectively) illustrate an exemplary implant that includes a main body and a sensor.
Figure 11B:
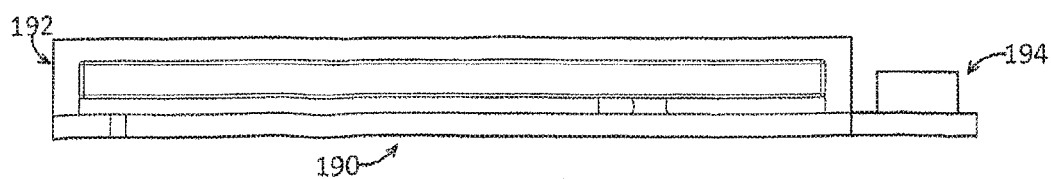

FIGS. 11A and 11B (top and side views, respectively) illustrate an alternative implant 190, which includes main body 192 and sensor 194. Main body 192 can include any of the components set forth herein. Width W of the body 192 is wider than in FIGS. 9 and 10, and sensor 194 is oriented degrees relative to the sensor in the embodiment in FIG. 9A. Implant 190 can also be adapted such that sensor 194 can rotate with respect to main body 192. In some exemplary embodiments the sensor has a width that is about 0.3 mm to about 2 mm, such as from 0.5 mm to about 1.5 mm.

FIGS. 12A-12F illustrate an exemplary implant 200 that has more of a square configuration that embodiments above. At least a portion of the implant has more of a square configuration, even if there are one or more arms extending from a main body portion.

Implant 200 includes an outer cover 210 and internal portion 220. Any of the description herein relative to covers can also apply to cover 210, and any of the components described above can also be included in internal portion 220 (e.g., battery, processor, antenna, etc.). For example, internal portion 220 can include any or all of the components found in internal portion 140 shown in FIG. 8A, but they are organized within the implant in a different manner.

Figure 12A:
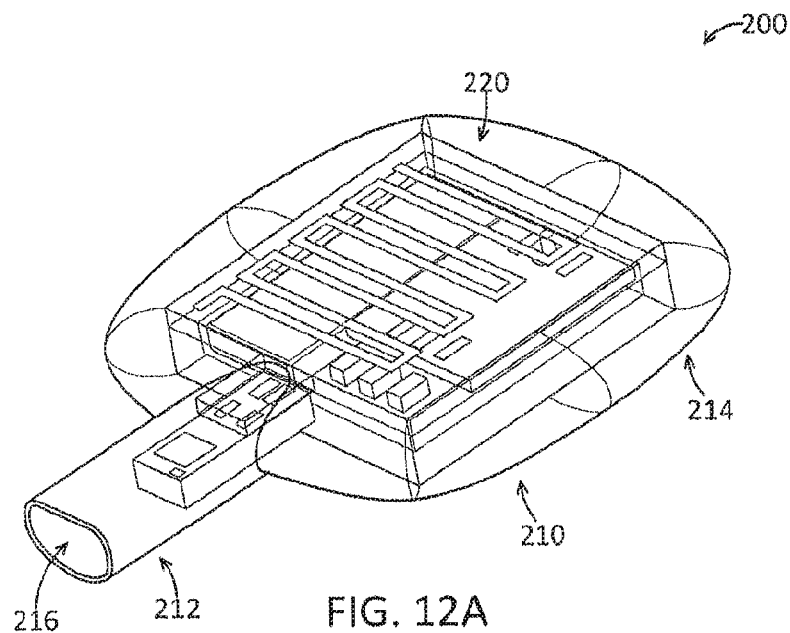
Figure 12B:
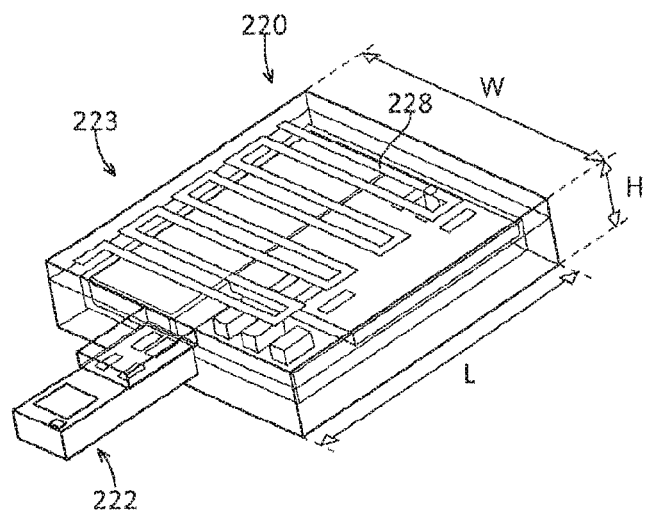

Figure is a bottom perspective view with the cover 210 on internal portion 220. FIG. 12B is the same view from FIG. 12A without cover 210. FIG. 12C is a front view of internal portion 220 without cover 210. FIG. 12D is a bottom view without cover 210. FIG. 12E is a top view without cover 210. FIG. 12F is a top view including cover 210. FIG. 12G is a front view including cover 210.

Internal portion 220 includes a main body portion 223 from which sensor 222 extends. The square configuration can make it easier to implant the implant in certain places in the eye. Main body portion 223 has a square configuration, with Length L and width W being the same dimensions. Body portion 223 can have, however, slightly rectangular configurations as well. Cover 210 similarly has a main body portion 214 with a generally square configuration and an arm portion 212 extending therefrom. Arm 212 has an open end defining lumen 216 so pressure sensor 222 can communicate with the environment.

Internal portion includes bottom housing 221 and top housing 225 (see FIG. 12C) that interface at a hermetic seal, examples of which are described herein. The internal portion also includes antenna 228 disposed in the bottom portion of the internal portion 220, battery 224, pressure sensor 222, processor 226 (e.g. ASIC), and electrical connect or via 227.

Other aspects of any of the embodiments herein can similarly apply to implant 200.

It is essential to provide a hermetic seal around the whole implant in order to ensure long term biocompatibility and also eliminate the risk of ocular fluids coming in contact with the miniature electronic circuit boards comprising the implant, potentially causing short circuits and other failures, including corrosion. In some embodiments, a hermetic seal may be formed by encasing the whole implant in a non-permeable material such as glass or Titanium, then closing the casing by means of laser welding, anodic bonding, or other types of sealing process that causes localized heating and fusion but does not cause a significant rise in temperature of the contents of the implant, for example, less than 2 degrees C. A challenge arises when designing a hermetic seal for a pressure sensor module, since it is necessary for the anterior humor of the eye to transmit its pressure to the sensor element inside the hermetically sealed implant in order to obtain reliable measurements of IOP.

Figure 13:
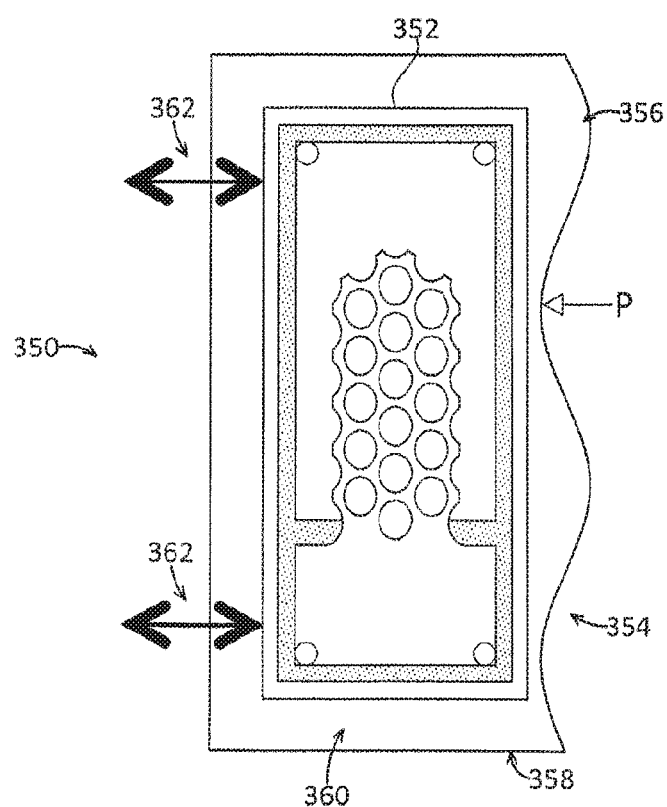
FIG. 13 illustrates a portion of an exemplary implant in which a pressure sensor is hermetically sealed inside a fluid chamber.

FIG. 13 illustrates a portion of an exemplary implant 350 in which pressure sensor 352 is hermetically sealed inside chamber 354. This concept of a fluid-filled chamber in which a pressure sensor is disposed can be incorporated into any implantable device herein. Chamber 354 includes a casing 358 and thin flexible membrane 356, which together define an outer wall of the implant. The implant also includes vias 362 that electrically connect pressure sensor 352 to other implant electronics, as described elsewhere herein. The chamber also includes inert fluid 360 contained within the chamber 354. Thin flexible membrane 356 is thin and flexible enough that it will transmit pressure P exerted by the anterior humor to fluid 360 within the chamber, which transmits the pressure to pressure sensor 352. In some embodiments flexible membrane 356 can be between 2 microns and 50 microns, such as 2-25 microns, such as such as 2-20 microns, such as 2-15, such as 2-10 microns, such as 5-10 microns. In some embodiments flexible membrane can be made of titanium or parylene. In some embodiments casing 358 can be made of titanium (e.g., TiN) or glass, and optionally coated with ceramic, examples of which are described herein. Examples of fluid 360 include, without limitation, nitrogen and silicone oil. The remainder of implant 350 can be the same as any of the other implants described herein.

In some embodiments the sensor comprises a piezoelectric sensing element where an inert fluid in the fluid chamber transmits hydrostatic pressure to the sensing element through the flexible membrane. In some embodiments the sensor comprises a capacitive sensing element wherein an inert fluid in the fluid chamber transmits hydrostatic pressure to the sensing element through the flexible membrane.

Any of the implants herein can have an unfolded length between about 2 mm to about 20 mm, such as between 2 mm and 15 mm, such as between 3 mm and 10 mm, such as about 7 mm. The housing can have a length of between 1 mm and 8 mm, such as between 1 mm and 7 mm, such as between 1 mm and 6 mm, such as between 2 mm and 5 mm, such as about 3 mm, or 3.3 mm.

The implants herein should be easy to surgically implant, and can optionally be implanted using a scleral tunnel or a clear corneal incision of perimeter less than 5.0 mm, optionally using a punch incision with a needle of outer perimeter preferably less than 1.2 mm, more preferably less than 1.0 mm. The implant should have long term biocompatibility, should not cause tissue erosion, should not cause the loss of corneal endothelium, and should not touch the iris, which will lead to deposition of iris pigment. The implants should provide a routine explanation option. The implants are preferably implanted in the sclera, or the conjunctiva, with the sensor being placed in the anterior chamber, posterior chamber, or inside the lens capsule as in the form of a capsular ring, while it may also be attached to an intraocular lens, the iris, the ciliary bodies, or be sutured to the ciliary sulcus.

In some embodiments the overall implant dimensions are less than 4.0 mm×1.5 mm×1.0 mm, preferably less than 3.5 mm×1.5 mm×1.0 mm, more preferably less than 2.5 mm×2.5 mm×1.0 mm, and most preferably less than 2.5 mm×2.5 mm×0.500 mm.

Any of the implants herein can have a folded length (after a portion of the implant is folded, or bent) between about 1 mm and 15 mm, such as between 1 mm and 12 mm, such as between 2 mm and 10 mm, such as between 3 mm and 9 mm, such as between 4 mm and 8 mm, such as between 5 mm and 7 mm, such as about 6 mm.

Exemplary pressure sensor dimensions can be 0.5 mm-1.5 mm×0.5 mm-2 mm. Off-the-shelf pressures sensors may be used in some embodiments.

Any of the implant housings herein, such as bottom housing 221 and top housing 225 in FIG. 12C (which may also be referred to as "casing" herein) can in some embodiments comprise glass or titanium with a gold or titanium plating (or any other biocompatible metal coating). The flexible connector, in embodiments that include one, can be a variety of suitable materials, such as, without limitation, a polymeric material encapsulated in a biocompatible silicone elastomer. The pressure sensor portion of any of the implants can include a sensor flexible membrane (e.g., Glass/Silicon), with other sides encapsulated in a silicone elastomer. In some embodiments the implant can have a parylene C coating on sensor membrane edges.

In any of the embodiments, any of the housings, such as a top housing or a bottom housing, can have a wall thickness of about 25-200 microns, such as about 50-150 microns, or about 75-125 microns, or about 100 microns. The wall thickness can provide hermeticity over a 10 year lifetime. Any of coatings herein can be about 0.1 micron to about 50 microns, such as about 1 micron to about 25 microns. The housings can comprise bonded top and bottom portions interfacing at a seal, as shown. The housings can have any of the following exemplary general shapes or configurations to provide a delivery profile that enables 1.0 mm external diameter: square, oval, circular, C-shaped, rectangular, chamfered, etc. The housings in FIGS. 5A and 5B, for example, have outer surfaces that are C-shaped, which allows the device to have a smaller profile than it would have with, for example, a more rectangular configuration.

Figure 14A:
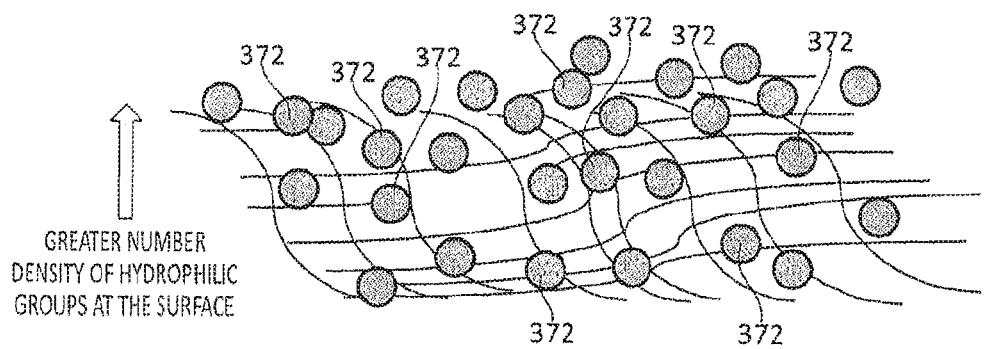
FIGS. 14A and 14B illustrate that some exemplary implants can be coated with a biocompatible coating that may be optionally infused with weakly bonded to an anti-inflammatory agent or an anticoagulant.
Figure 14B:
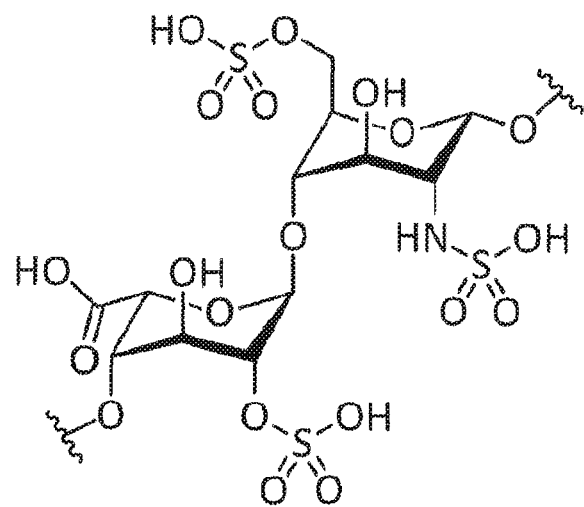

In some embodiments the implant is coated with a biocompatible coating that may be optionally infused with weakly bonded to an anti-inflammatory agent or an anticoagulant, which is illustrated in FIGS. 14A and 14B. The coating can be comprised of a cross-linked amphiphilic polymer with hydrophobic and hydrophilic segments. Typical polymers include hydrogels, silicone hydrogels and the like, with equilibrium water content ranging from 30% to 90% by weight. The cross-linked polymer comprising the coating folds such that the number density of hydrophilic groups increase towards the outer surface of the coating, while the surface contacting the implant may be richer in hydrophobic groups (see Gandhi, A, et al, "Studies on thermoresponsive polymers: Phase behaviour, drug delivery and biomedical applications" in Asian Journal of Pharmaceutical Sciences, 2015; pp 107). This coating may include hydroxyl groups, amino groups, amides, sulfhydryl groups, thiols, as well as ionic moieties such as ammonium groups, alkyl ammonium groups and the like. Thermoresponsive polymers such as Poly(N-isoropyl acrylamide and homologues may also be used. These groups on the cross linked network comprising the coating are used to hydrogen bond or electrostatically bond anticoagulants such as Heparin sulfonate. FIG. 14A shows anti-inflammatory agents or anticoagulant groups 372, with the remainder of the groups being hydrophilic groups. An example of an anticoagulant is heparin, which is 13-20 kDa.

The hydrogel layer can have a gradient in number density of hydroxyl groups, wherein the gradient is in the opposite direction of the gradient in cross-link density.

The outer surface of the coating may be patterned or textured in order to promote fixation into the muscle in which the implant is positioned. The design of the texture is optimized to cause a minimal level of fibrosis causing adhesion of tissue to the implant without unduly enhancing immune response to the implant or chronic inflammation. Table 1 includes examples of components that may be included in such coatings.

The outer layer of the coatings may have pendant side chains that have considerable local chain mobility that function as celia, further inhibiting attachment and denaturation of protein and cell membranes.

TABLE 1

| Hydrophilic Monomers | Hydrophobic Monomers | Cross-Linking Agents | Anticoagulants |
| --- | --- | --- | --- |
| Hydroxyethyl methacrylate | Methyl methacrylate | Ethylene Glycol dimethacrylate | Heparin |
| Glyceryl monomethacrylate | Styrene | Bis Acrylamide | Antithrombin |
| Acrylic acid | Furfuryl acrylate | | Direct thrombin inhibitors lepirudin, desirudin, bivalirudin, argatroban. |
| Methacrylic acid | | | |
| N-isoprpylacrylamide | | | |
| Trimethylol propane triacrylate | | | |

The disclosure that follows relates to coatings that can be applied to implantable devices. In some embodiments the implantable devices are implantable ocular devices, such as intraocular lenses and/or IOP sensors. For example, the coatings below may be applied to any of the IOP sensors described elsewhere herein. But unless the disclosure below indicates to the contrary, the coatings here may be applied to a variety of implantable devices.

Intraocular implants are routinely used to treat a number of eye disorders, and include intraocular lenses ("IOLs"), glaucoma shunts, and drug delivery systems, such as the fluocinolone implant developed by B&L for treatment of chronic uveitis (Retisert), and Vitrasert®, a controlled-release intraocular implant that contains ganciclovir for treatment of Acquired Immunodeficiency Disorder and refractory uveitis. This non-biodegradable implant is composed of a ganciclovir tablet surrounded by a film made of Poly vinyl alcohol and ethylene vinyl acetate. The success of these implants depends partially on their ability to avoid long term immune responses causing chronic inflammation and fibrosis. The ciliary epithelium and the endothelium of capillaries within the ciliary body and the cornea form a physical and immunological barrier called the blood-aqueous barrier. The blood-aqueous barrier, along with other similar barriers throughout the eye, confers the properties of immune privilege to the intraocular environment. Immune privilege is believed to be an evolutionarily conserved trait that protects critical tissues from inflammation due to injury or infection.

A biocompatible coating designed for an implantable device should, first of all, be composed of materials that have biocompatible or non-toxic molecular structures. Other factors to consider for coatings may include degree of transparency, the refractive index of one or more parts of the coating, permeability, shear strength, and strength of adhesion to one or more surfaces of the implant. These factors may limit the choice of constituent chemicals and/or monomers for the formulation of the coating. A coating formed from such chemicals should be non-toxic, especially when it is extracted to remove all starting chemicals, after it has been polymerized in place. However, lack of toxicity alone does not guarantee long term biocompatibility of a coating. Arguably, there is no such thing as an "inert biomaterial." Upon implantation, such biomaterials, usually of synthetic composition, are subjected to a series of well-defined processes characterized as the foreign body reaction that ultimately leads to fibrous encapsulation of the implant. Implanted devices (e.g., implanted medical devices) are often isolated from the body by a dense collagenous capsule, which has long been an acceptable form of "biocompatibility" both by regulatory and historical standards. However, the inability to interface with normal host tissue as a result of the intervening fibrous tissue eventually leads to diminished function for devices that require close contact with, for example, parenchymal cells or neurovascular structures. The fibrotic tissue can thus diminish the functionality of certain implantable devices over time by preventing necessary a desired interface between one or more parts of the device and the host tissue.

The wound healing response can be generally described as four stages with varying degrees of overlap: hemostasis, inflammation, proliferation and remodeling. Following trauma, blood enters the wound site and clots, resulting in hemostasis. Inflammation at the wound-site begins as polymorphic neutrophils enter and phagocytize bacteria, foreign debris and damaged tissue before undergoing apoptosis. Macrophages subsequently enter the wound-site and continue the inflammatory reaction, while stimulating angiogenesis, the growth of new capillaries and the beginning of the proliferation phase, by secreting platelet-derived growth factor (PDGF) and TGF-β. The proliferation phase is named for the proliferation of fibroblasts and characterized by the rapid deposition of collagenous ECM throughout the wound bed, which is eventually reoriented and further modified in the remodelling phase. Typically, the wound-healing response results in a resolved wound with no further activity. However, in the case of an implanted biomaterial, low levels of inflammation persist indefinitely in a process known as the foreign body reaction. This unique reaction is driven primarily by the macrophage and their multi-nucleated successor, the foreign body giant cell. The key to modulating the foreign body reaction, then, is to modulate the interaction between macrophages and material. To be truly biocompatible, a coating should not induce an avid immune response that may lead to extensive fibrosis, nor should it cause cell apoptosis through strong surface interactions that can lead to irreversible binding of the cell membrane to the surface of the coating.

In general, two strategies exist to develop a biocompatible coating. The surface of the coating is designed to minimize adhesion of cells present in the surrounding environment, including macrophages. For example, cortical and epithelial cells remain in the eye following extraction of a cataract lens. If these cells adhere to the surface of the implant, they may trigger an immune response leading to proliferation of these cells. Even when cells attach to the surface of the implant, this attachment is ideally reversible, with the cells retaining their round shape. The surface of the coating should also prevent attachment of proteins and smaller peptides. Even when attachment does take place, the energy of adhesion is minimized, so that the attached protein does not undergo denaturation. It is proposed that a particular range of cross-link density and a particular area density of hydroxyl groups is desirable to achieve these surface characteristics, identified as important requirements for biocompatibility. Differences in adhesion of macrophage on surfaces of hydrophobic and hydrophilic implants (e.g., intraocular lenses) have been reported by Pintwalla (Pintwalla, RC, "Development of an in-vitro model to assess wound healing response and biocompatibility of intraocular biomaterials", Thesis presented to the University of Waterloo, Ontario, Canada, 2014, pp 38). Pintwalla illustrates the surface of a pHEMA IOL observed on a confocal laser scanning microscope, illustrating the adhesion of macrophages to the surface of the lenses.

Hydrogel implants have also been evaluated for their ability to modulate the immune response. Pintwalla. Id. Pintwalla examined the uveal biocompatibility of PMMA and pHEMA IOL materials by quantifying cellular activation by examining expression of the cell-surface adhesion protein CD54 (or ICAM-1) on macrophages in vitro. CD54 has been shown extensively in the literature to be upregulated on macrophages in response to inflammatory stimuli, including a strong correlation in vivo between CD54 upregulation and increased production of TGF-β1. Following 2 days exposure to an IOL, Pintwalla observed significant increases in expression of CD54 on macrophages cultured with a hydrophilic acrylic (pHEMA) IOL compared to cells cultured on TCPS, suggesting that hydrophilic acrylic materials may cause significant macrophage activation compared to hydrophobic acrylic materials. Macrophages exposed to a pHEMA IOL showed signs of significant activation but an inability to strongly adhere to the IOL surface.

Coatings can include chemicals and can be adapted for slow and sustained release thereof that inhibit expression of certain critical cytokines that mediate the foreign body reaction process. For example, Poly(ethylene glycol) ("PEG") hydrogels containing a peptide mimic of the TNFα recognition loop on the TNF-receptor 1 were evaluated as a cell encapsulation material (Dziki, J L, et al, "Extracellular matrix bioscaffolds as immunomodulating biomaterials", in *Tissue Engineering, Part A*, 2017; vol 23, part 19, 20, pp 1152-1154). Because these hydrogels could sequester TNFα, encapsulated cells were protected from this pro-inflammatory cytokine. Similarly, PEG hydrogels containing an inhibitory peptide for the IL-1 receptor were able to protect encapsulated islet cells. Attempts to combine controlled-release technologies and biomaterials to alter the host immune microenvironment and promote better cell engraftment have also been investigated in preclinical animal studies with success.

The disclosure is related to biocompatible implant coatings that can comprise an inhibitor of the cytokine TGFβ, which is widely implicated as being a central mediator of the fibrotic response. TGFβ is present in the aqueous humor of the eye and exists largely in a latent, inactive form. Under normal conditions, TGFβ activity is tightly regulated by proteins in the aqueous humor such as 2-macroglobulin, which have a high affinity for free active TGFβ. Following trauma to the eye, e.g. surgery or insertion of an implant, active levels of TGFβ can be elevated. Eked, J A, et al, "The lens as a model for fibrotic disease", in Phil Trans R Soc, 2011; 366, pp 1301, illustrates a pathway for transformation growth factor (TGF β) to stimulate fibrotic events, where FGF is fibroblast growth factor, Coll is collagen, SMA is smooth muscle actin, and FN is fibronectin.

Data has shown that while a hydrophilic coating leads to a reduced adhesion of cells and proteins on the implant surface, macrophage freely circulating in the ocular environment cause significant up-expression of inflammation-inducing cytokines, such as TGFβ. Inflammation caused by the foreign body reaction (described above) induced by the implant cannot be controlled by simply providing a drug eluting implant that releases anti-inflammatory drugs in a slow and sustained manner. There is evidence in literature that such anti-inflammatory drugs do not have an appreciable effect in reducing the incidence of fibrosis, or the size and growth rate of the fibrotic capsule that cocoons the implant. Anti-inflammatory drugs may nevertheless be critically required in a controlled release regiment for other benefits in the healing eye, for example they may reduce incidence of angle closure or hyphema. Similarly, addition of pressure controlling drugs into the formulation may be beneficial for other benefits, particularly for patients with an elevated intraocular pressure.

Figure 15:
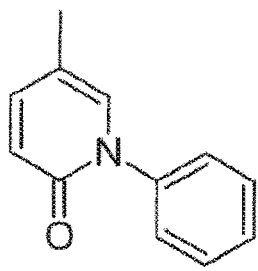
FIG. 15 shows the molecular structure of Pirfenidone.
Figure 16A:
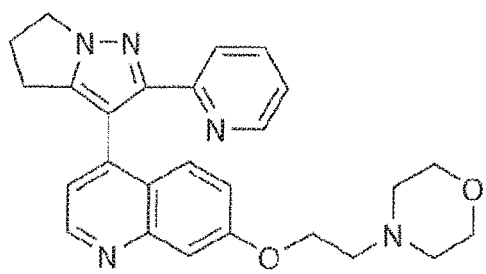
FIG. 16A shows the chemical structure of a chemical that inhibits the expression of TGF-β.
Figure 16B:
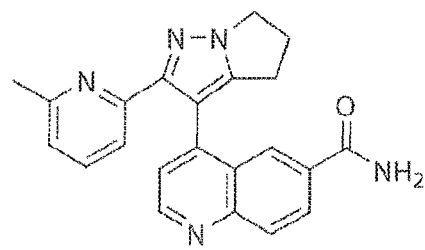
FIG. 16B shows the chemical structure of a chemical that inhibits the expression of TGF-β.

In some particular embodiments, the implantable device coatings herein are hydrophilic, have minimal tendency to cause cells to adhere to their surface, and are adapted so that they release one or more chemicals that inhibit expression of critical cytokines, such as TGF-β. One particular example of a chemical that inhibits expression of critical cytokines is Pirfenidone, the molecular structure of which is shown in FIG. 15. Pirfenidone is an inhibitor for TGF-β production and TGF-β stimulated collagen production, and it reduces production of TNF-α and IL-1β, and also has anti-fibrotic and anti-inflammatory properties. Another exemplary chemical that can be incorporated into any of coatings herein to inhibit expression of critical cytokines is Galunisertib, a potent TGFβ receptor I (TORI) inhibitor, the chemical structure of which is shown in FIG. 16B. Another exemplary chemical that can be incorporated into any of coatings herein to inhibit expression of critical cytokines is LY2109761, which is a selective TGF-β receptor type I/II (TβRI/II) dual inhibitor, the chemical structure of which is shown in FIG. 16A. Galunisertib and LV 2109761 are commercially available from Selleck Chemicals.

In some preferred embodiments Pirfenidone is incorporated into the coating, with a primary function to inhibit the expression of TGF β.

Other pharmaceuticals can also be incorporated into coatings herein, any of which can be incorporated in any combination with other agents. The following list includes other pharmaceuticals that can also be incorporated into coatings herein: heparin, both low and medium molecular weight to control fibrosis and provide anticlotting functionality; steroids; anti-inflammatories such as dexamethasone, or other corticosteroids; Cox 1- and Cox-2 inhibitors to control inflammation; intraocular pressure reducing agents such as beta blockers and carbonic anhydrase inhibitors.

Prednisolone, the molecular structure for which is shown in FIG. 17, is a water soluble powder. Prednisolone is an example of a steroid that can be incorporated into coatings herein and adapted to be released over time. With its release, depressed production of eosinophils and lymphocytes occurs, but erythropoiesis and production of polymorphonuclear leukocytes are stimulated. Inflammatory processes (e.g., edema, fibrin deposition, capillary dilatation, migration of leukocytes and phagocytosis) and the later stages of wound healing (e.g., capillary proliferation, deposition of collagen, cicatrization) are, however, inhibited. μRecommended dosage levels are in the range of 0.1 mg/kg of body weight. In some embodiments there is a release rate of at least 0.01 μg/hour.

Since the total weight of the coatings herein is generally in the range of $4-6 \times 10^{-4}$ g, a 10% loading of a cortico steroid (e.g., Prednisolone) provides an average life of 500 hours.

The coatings herein are preferably hydrophilic coatings, ensuring that adhesion of cells and protein is kept at a minimum. Preferably, the coatings incorporate drugs and/or other agents that are released at a sustainable rate ranging from a period of 1 week to 6 months. The coatings comprise inhibitors of fibrosis, including, by example only, TGF-β, other cytokines expressed as mediators of the inflammatory cascade, SMA, and/or integrins.

The hydrogel coatings preferably form a scaffold that can support an extracellular matrix, and have a multilayered structure. Such a hydrogel coating may be, for example, a polyacrylate, a polymethacrylate, a polyurethane, a polyether, a polyester, a polyvinyl compound, a polycarbonate, or an epoxide.

In some preferred embodiments, the coating includes pendant hydroxyl groups, with the number density of hydroxyl groups varying between the layers of the coating. Preferably the number density is the lowest in the layer closest to the surface of the implant (i.e., the innermost layer of the coating) and highest at the uppermost layer of the coating.

In some preferred embodiments, the coatings herein have first, second, and third layers (which includes embodiments in which there are no more than three layers). FIG. 19B illustrate an exemplary embodiment in which an implant is coated with a coating, wherein the coating includes first inner layer 300, second intermediate layer 302, and third outermost layer 304. The implant can be any of the implants described herein, an outer surface of which is coated with the coating. The innermost layer may be either infused with pharmaceuticals or incorporating solid but bioerodable particles loaded with a mixture of pharmaceuticals. The second, or central, layer, which can be the thinnest of the three layers, may be hydrophilic or hydrophobic in chemical composition, and functions as a partial barrier to the pharmaceutical molecules, adapted to cause a slow and sustained release of the releasable components from the first layer through the second and third layers and into the ocular medium outside the implant. The third or the uppermost layer is most highly hydrophilic of all three, has the desired area density of pendant hydroxyl groups for minimal cell adhesion, and highest water content. Such multilayer coatings may either function as a biocompatible coating by itself, or it may be infused with pharmaceuticals in order to inhibit TGF β, or other activators of the inflammatory cascade.

In some preferred embodiments, at least one of the three layers may comprise polyethylene glycol ("PEG") oligomers of different end groups and different molecular weights. For example, polymerized samples of PEG oligomers of different molecular weights have different crystallinities, hence widely different permeability and solubility properties. These properties can be used to control the rate of release of the pharmaceuticals in the coating that are required for biocompatibility. Hirayama, et al, reported a study of permeability and solubility of PEG oligomers of different molecular weights and end groups, which is incorporated by reference herein (Hirayama, Y, et al, "Permeation properties to $CO_2$ and $N_2$ of polyethylene oxide containing and cross-linked polymer films", in Journal of Membrane Science, 1999; 160, pp 87-89). FIGS. 18A and 18B illustrate exemplary mono and dimethacrylate derivatives of PEG oligomers, respectively, that may be incorporated into one or more layers of the multilayered coating structures herein.

The Examples below provide exemplary details of exemplary coatings that may be used to coat implantable devices described herein.

EXAMPLES

Formulations I to V in Table 2 were prepared from commercially available starting materials. Molecular weights of the PEG oligomers were in the range of 1,000 to 5,000 Daltons in these examples, and preferably in the range of 2,000 to 4,000 Daltons. For each exemplary formulation, the table includes an exemplary application (e.g., layer) in a multilayered coating. The percentage shown are percentages by weight.

TABLE 2

Monomers used in Example polymer coatings

| Formulation No | Monomers (Weight Per cent) | | | | | |
|---|---|---|---|---|---|---|
| | Mono-functional | Di-functional | Tri-functional | Tetra-functional | Initiators | Coating Application |
| I | PEG Acrylate (30%); PEG Methacrylate (0%) | PEG Diacrylate (69%); PEG Dimethacrylate (0%) | Trimethylol propane Triacrylate (0%) | Pentaerythritol Tetraacrylate (0%) | TPO (1%) | Outermost layer |
| II | PEG Acrylate (30%); PEG Methacrylate (30%) | PEG Diacrylate (24%); PEG Dimethacrylate (10%) | Trimethylol propane Triacrylate (0%) | Pentaerythritol Tetraacrylate (5%) | TPO (1%) | Inner layer |

TABLE 2-continued

Monomers used in Example polymer coatings

| Formulation No | Mono-functional | Di-functional | Tri-functional | Tetra-functional | Initiators | Coating Application |
|---|---|---|---|---|---|---|
| III | PEG Acrylate (20%); PEG Methacrylate (20%) | PEG Diacrylate (20%); PEG Dimethacrylate (20%) | Trimethylol propane Triacrylate (9%) | Pentaerythritol Tetraacrylate (0%) | TPO (1%) | Inner layer |
| IV | PEG Acrylate (40%) PEG Methacrylate (10%) | PEG Diacrylate (31%) PEG DiMethacrylate (10%) | Trimethylol propane Triacrylate (0%) | Pentaerythritol Tetraacrylate (8%) | TPO (1%) | Middle Layer |
| V | PEG Acrylate (40%); PEG Methacrylate (10%) | PEG Diacrylate (24%); PEG DiMethacrylate (20%) | Trimethylol propane Triacrylate (0%) | Pentaerythritol Tetraacrylate (5%) | TPO (1%) | Outer layer |

For all of the formulations in Table I, the monomers were de-areated, mixed in the stated proportions, and maintained in a room lit with light of wavelength greater than 500 nm within a clean room (p<100), under an atmosphere of dry $N_2$. The implant (which can be, for example, an IOL that includes an integrated IOP sensor) was exposed to an oxygen plasma for about 10 minutes in order to generate oxides at the surface of the implant, then dipped into the monomer mixture for the first layer, allowed to drain excess monomer, then exposed to UV light ($\lambda \sim 405$ nm) for a period of 1-2 minutes, turning the implant continuously during this time. This operation was carried out under dry Nitrogen. Once the cure was complete for the first layer, the formation of the second layer was then initiated. The implant coated with the first layer was then dipped into a second monomer mix using the same methods as the first layer, and the second layer was thus formed. This process was continued until the three layers were formed on the implant.

Once the requisite number of layers had been deposited, the implant was then soaked in warm (~35 C) deionized water for up to 1 hour in order to remove all unreacted monomers. The implant was then placed in a fresh supply of deionized water, left immersed for 30 minutes, and then an aliquot was removed from the water, and analyzed by HPLC or GPC for unreacted monomers. The implant was then released for the next step once no monomers could be detected in the eluting medium. The implant was then dried under nitrogen for a period of 1 hour in order to partially dehydrate the coating prior to packaging. The equilibrium water uptake of the overall coating can be 20-80%, and in some preferred embodiments 35-75%. The coating can be left with about 10% to 30% water by weight (preferably 10-15%) after the final drying step.

Pharmaceuticals are incorporated into one of the inner layers of the coatings herein, preferably the innermost layer. The pharmaceuticals can be mixed with liposomes, liposome-cyclodextrin complexes, or PEG oligomers (PEG molecules in the molecular weight range of 20,000-50,000), lyophilized, then added to the appropriate monomer mix, mixed by mechanical stirring, then used to form the coating, as set forth in the manufacturing methods set forth above related to Table 2. It is generally desired to monitor the area density of hydroxyl groups on the surface of the coating. An optional but preferred value is 2 hydroxyl groups per repeating unit in the polymeric network that provides opportunities to form cyclic hydrogen bonded complexes with attaching groups. Depending on the folding pattern of the polymer chains that comprise the coating, a range of 1-3 hydroxyl groups per repeating unit exist in some embodiments.

Table 3 provides some, in some embodiments preferred, properties for coatings or coating constituents herein. Any of the coatings herein can include one or more of these properties, unless specifically indicated to the contrary herein.

TABLE 3

| Property | Range | Preferred range |
|---|---|---|
| Biocompatibility | No aromatic content | Low aromatic or alicyclic content |
| Glass Transition Temperature | −50 C. to 20 C. | −10 C. to 0 C. |
| Equilibrium water Uptake | 25% to 90% | 35% to 75% |
| Elongation at break | 5% to 250% | 30% to 150% |
| Hydrophilicity | Water contact angle: 0° to 65° | Water contact angle: 0° to 30° |
| Crystallinity | 0% to 50% | 0% to 20% |
| Molecular weight of monomer | 250-50,000 | 500-20,000, such as 350-1500 |

While PEG is described in some embodiments herein, monomers other than PEG may also be used to develop one or more layers of the coating. The following are additional examples of monomers that can be used to form one or more layers of the coating: PEG monofunctional and difunctional monomers, terminated with acrylates, methacrylates, vinyl groups, isocyanates, thiols, epoxides, acyl chlorides and amines; other hydroxylated or hydrophilic monomers including for example only, trimethylol propane tetraacrylate, pentaerytritol tetraacrylate, glyceryl monomethacrylate, ethoxylated trimethylol propane triacrylate, acrylic acid, N,N'dimethyl acrylamide, aminoethyl methacrylate, N,N'dimethyl bisacrylamide, polyethylene oxide, polyvinyl alcohol; non functionalized PEG oligomers, in the molecular weight range 10,000-50,000; and/or vinyl anisole or vinyl phenol.

The different layers need not be made up of the same monomers or monomers by weight, but rather can comprise different monomers.

In some embodiments the total thickness of the implant coating is in the range of 50-200 microns, and in some preferred embodiments from 100-150 microns. Any of the individual layers in the coating can have a thickness of 5-100 microns, and in some preferred embodiments from 15-50 microns. In some embodiments the central layer is the thinnest layer, which is described elsewhere herein.

The outermost surface of the implant coating (i.e., the outermost surface of the outermost layer) is, in some preferred embodiments, textured so as to provide optimum adhesion to the surrounding tissue without creating risk of fibrosis. The textured outer surface can include a plurality of depressions, each of which may have a height between 5 microns and 15 microns, such as 7.5 microns and 12.5 microns, such as 10 microns.

PEG-based polymeric gels may also be used in the coatings herein as encapsulating media of pharmaceuticals, which are adapted to be released over time. These gels, in some preferred embodiments, can be held together as a cross-linked network by chemical bonds that are susceptible to a slow hydrolytic cleavage reaction under use conditions, rendering the gel bioerodable. One example is the PEG based gel developed as a resorbable surgical sealant by Baxter (Co-seal) (Wallace, T G, et al, "A tissue sealant based on reactive multifunctional polyethylene glycol", in J Biomed, 2001; 58, pp 545-555.) This gel resorbs in-vivo in about 1 week. This or similar gels made of cross-linked PEG based network polymers may be pre-mixed with pharmaceuticals prior to cross-linking and gel formation, then added as an additive to one of the two inner coating layers, exemplary methods of manufacture of which are described elsewhere herein. Other types of delivery agents may be used, preferably liposomes, and more preferably liposomes comprising cyclodextrins or chitosan, especially for delivery of hydrophobic materials (Gharib, R., et al, "Liposomes incorporating cyclodextrin-drug complexes: Current state of knowledge", in Carbohydrate Polymers, 2015; 129, pp 175).

Any of the coatings herein can be applied to implantable devices, such as the ocular implantable shown in FIGS. 1, 2 and 3. The devices can be coated with any of the coatings set forth herein using any of the exemplary methods of manufacture herein, such as the methods described with reference to the formulations in Table 2.

In some embodiments herein, any of the coatings herein can be used to coat intraocular lenses that are placed in a capsular bag after the native intraocular lens has been removed (e.g., due to cataracts). Intraocular lenses have been in use since 1948 when they were first introduced by Dr. Harold Ridley at Moorfield hospital to treat patients with cataracts. Initially, most IOLs were made of a hard, hydrophobic transparent plastic material, namely polymethyl methacrylate. Starting in 1988, new materials were introduced for fabrication of IOLs, namely cross-linked silicone and acrylic elastomers, so that IOLs could be folded prior to implantation enabling a reduction of the size of the incision required to insert the IOL into the capsular bag. Long term efficacy of these implants partly depends on their ability to avoid long term immune responses causing chronic inflammation and fibrosis that may lead to posterior capsular opacification (PCO) through proliferation of lens epithelial cells or lens cortical cells.

More recently, hydrophilic materials have been used to fabricate IOLs. These include cross-linked networks of acrylate elastomers that have an equilibrium water content in the range of 10% to 30% by weight. These materials are highly elastic, with a high value of elongation at break, enabling the IOLs to be folded to a small profile prior to implantation. Incision sizes of 2.8 mm or less have been used to implant IOLs of 6.0 mm in diameter, by using these materials.

Two factors influence selection of IOL design and material: reducing the possible incision size so that it is small as possible, and minimization of postoperative inflammation and fibrosis. Arising out of these two factors are the major drivers of materials development for IOLs—foldability and high refractive index, since a higher refractive index enables use of thinner IOLs of flatter surface curvatures even for extreme values of the axial length of the eye.

The ciliary epithelium and the endothelium of capillaries within the ciliary body and the cornea form a physical and immunological barrier called the blood-aqueous barrier, which is described above and protects critical tissues from inflammation due to injury or infection. Another post-surgical complication that can affect up to 20% of patients currently undergoing cataract surgery is occurrence of dysphotopsia. There are two types of dysphotopsia that can occur after cataract surgery. Dysphotopsia refers to an unwanted image that patients see after cataract surgery. Positive dysphotopsia is unwanted light, such as a streak, starburst, flicker, fog or haze, while negative dysphotopsia is a black line or crescent in the far periphery of patients' vision. Dysphotopsia is believed to be caused by internal reflection of off axis rays from the posterior surface of the IOL, sometimes exacerbated by edge design (e.g., square edge design) that may enhance this unwanted light scattering effect.

It is clear that while state of the art IOLs have been shown to be non-toxic, they still have long term biocompatibility issues, as shown by their tendency to promote PCO and fibrosis. At the same time, use of materials with high refractive index ($>1.52$ at 530 nm) increases the risk of dysphotopsia.

The disclosure below generally refers to coatings for IOLs that can be applied to both hydrophobic and hydrophilic materials, and that reduce the risk of dysphotopsia and fibrosis. A biocompatible coating designed for an IOL should, first of all, be composed of biocompatible or non-toxic molecular structure. Other design constraints that may also be imposed include one or more of transparency, a particular refractive index, permeability, shear strength, and strength of adhesion to the surface of the implant. One or more of these design constraints may limit the choice of constituent chemicals, or monomers for the formulation of the coating. A coating formed from such chemicals should be non-toxic, especially after it has been extracted to remove all starting chemicals, after it has been polymerized or cross-linked in place. However, lack of toxicity alone does not guarantee long term biocompatibility of a coating. Arguably, there is no such thing as an "inert biomaterial." Upon implantation, such biomaterials, usually of synthetic composition, are subjected to a series of well-defined processes characterized as the foreign body reaction that ultimately leads to fibrous encapsulation of the implant. This process is especially acute in animals with a more acute immunological response than humans, such as canines. Household canine pets in USA are prone to develop cataract and some species develop congenital cataracts routinely. Increasingly, they are being prescribed to undergo cataract surgery and IOL implantation. We believe that an IOL rendered biocompatible and tolerated in a canine eye with minimal, controlled fibrosis will also be useful for human patients, especially those who have a compromised blood aqueous barrier, such as those suffering from diabetic retinopathy or uveitis.

The coatings for an intraocular lens may be any of the coatings described above. One or more additional and optional aspects for IOL coatings may, however, be included below. The description that follows does not necessary apply to the coatings described above, which can be applied to a variety of implantable devices. Aspects of coatings that may be more suited for IOLs may be referred to below as an "IOL coating" or a derivative thereof. IOL coatings disclosed below can have a multilayered structure with an outer layer being highly hydrophilic, designed for minimizing cellular adhesion. An inner layer is less hydrophobic with a higher cross-link density, preferably some crystallinity, less permeability, higher shear modulus than the outermost layer, a moderate tensile modulus, and an elongation at break exceeding 100%. The outermost layer may additionally be patterned to reduce cellular adhesion. The IOL coatings are transparent, and have relatively low refractive indices. Optionally, the cross-link density is optimized to allow long range segmental diffusion within each sublayer, but not across layers.

The IOL coatings can include one or more of the following properties: transparent with less than 10% absorption of light in the wavelength range 400-750 nm; a refractive index in the range from 1.44-1.50 at 530 nm; an outer layer with a number density of hydroxyl groups of at least $10^4$ per micron square; an equilibrium water content of at least 50% (and in some preferred embodiments at least 70%, such as from 70%-99%); a cross-link density less than 1 M/L, and a free volume fraction of more than 10%, and a tensile modulus less than 0.1 MPA.

In some preferred embodiments, IOL coatings include at least two layers each having different cross-link densities, two different refractive indices, and other physical properties. FIG. 19A illustrates an exemplary coating on an implant, where the coating includes first inner layer 200 and second outer layer 202. Preferably, the outer layer has a lower refractive index arising from a lower cross-link density, a higher equilibrium water content and a greater volume fraction of free volume. A preferred range of refractive index of the outer layer is in the range of 1.39 to 1.44, while the inner layer has a refractive index in the range 1.44 to 1.50. This layer design is intended to minimize interfacial reflection of light, and hence minimize dysphotopsia. Preferably, the coating has a continuous gradient of cross-link density and hydration level such that the refractive index of the outermost layer is the lowest refractive index, optionally being lower than 1.40. Back reflection from an interface between two media of refractive indices n1 and n2 is given $(n_1-n_2)^2/(n_1+n_2)^2$.

Table 4 provides the percent light reflected back for an IOL without a coating and a coating of refractive index in the range of this disclosure. A two layer coating with a continuous change in refractive indices is modeled here.

TABLE 4

Back reflection from the anterior surface of a coated IOL and interfacial reflection

| Refractive index of Implant | Refractive Index of Coatings | Percent Back and Interface Reflection |
|---|---|---|
| 1.54 | None | 0.49%/NA |
| 1.54 | 1.47/1.41 | 0.054%/0.07% |

TABLE 4-continued

Back reflection from the anterior surface of a coated IOL and interfacial reflection

| Refractive index of Implant | Refractive Index of Coatings | Percent Back and Interface Reflection |
|---|---|---|
| 1.54 | 1.44/1.40 | 0.11%/0.05% |
| 1.50 | None | 0.41%/NA |
| 1.50 | 1.47/1.41 | 0.028%/0.07% |
| 1.50 | 1.44/1.40 | 0.073%/0.053% |

Table 4 shows that a ten-fold reduction in back reflection from the anterior surface of the IOL, is achieved when a coating of relatively low refractive index is applied. Interface reflections, potentially causing dysphotopsia, are reduced to 0.07% or less. A similar reduction in light reflection was achieved when a three or more layer coating were used.

The IOL-specific coatings can be infused with one or more pharmaceuticals that are adapted to inhibit development of a fibrotic capsule around the IOL, and proliferation of A and E cells in order to inhibit development of PCO. Layers of a coating comprising one or more pharmaceuticals is described in more detail herein. An exemplary preferred candidate for inclusion into the coating is Pirfenidone, described elsewhere herein. Its main function will be to downregulate expression of TGF β. TGF β is known to initiate an inflammation cascade leading to fibrosis, although it has also been shown to downregulate MHC class I antigens in normal cells.

Examples of other pharmaceuticals that can be incorporated into the IOL-specific coatings herein and adapted to be released (and any of which can be incorporated in any combination with other agents) include heparin, both low and medium molecular weight to control fibrosis and provide anticlotting functionality; steroids; anti-inflammatories such as dexamethasone, or other corticosteroids; cox 1- and Cox-2 inhibitors to control inflammation; and intraocular pressure reducing agents such as beta blockers and carbonic anhydrase inhibitors.

Prednisolone, which is described elsewhere herein, can be incorporated into any IOL-specific coatings.

Any of the other aspects of any of the coatings described above with regard to general implant coatings, including methods of manufacture, can be applied to any of the IOL-specific coatings herein.

Additional Examples. The following are additional examples of the disclosure herein.

An optionally autonomous, wirelessly connected, intraocular pressure sensing implant, wherein said implant is less than 3.5 mm in its longest dimension.

The implant of any of the additional examples herein wherein said implant has an internal rechargeable power source that can provide operating power for at least one half day (12 h) of operation.

The implant of any of the additional examples herein wherein said power source is a rechargeable battery.

The implant of any of the additional examples herein wherein said implant has power and data management integrated circuits that consume less than 50% of its stored power in resistive losses.

The implant of any of the additional examples herein wherein said implant utilizes at least one application specific integrated circuit for power and data management.

The implant of any of the additional examples herein wherein said implant comprises a sensor that senses intraocular pressure and collects pressure data more than once every 12 hours and no more than once every minute.

The sensor of any of the additional examples herein wherein said sensor operates at a frequency of 30 Hz or more.

The implant of any of the additional examples herein wherein said ASIC is controlled by firmware that is reprogrammable by an external unit via wireless communication of data subsequent to implantation of any of the implants herein.

The implant of any of the additional examples herein wherein said ASIC downloads data to said external unit that is programmed to receive said data.

The implant of any of the additional examples herein wherein said ASIC actuates commencement of wireless recharging from said external unit upon receipt of a trigger signal.

The implant of any of the additional examples herein wherein a trigger signal may be transmitted from an external unit.

The implant of any of the additional examples herein wherein said trigger signal may be generated inside said ASIC when the output voltage of said rechargeable battery of claim 3 drops below a threshold voltage that is above the voltage at which the battery shuts down.

The implant of any of the additional examples herein wherein said implant is rendered biocompatible by being hermetically sealed.

The implant of any of the additional examples herein wherein said sensor is periodically actuated by an ASIC.

The implant of any of the additional examples herein wherein a trigger can be externally or internally generated.

The implant of any of the additional examples herein wherein a trigger signal when internally generated, is reprogrammable.

The implant of any of the additional examples herein wherein data is processed and filtered in firmware in an ASIC.

The implant of any of the additional examples herein wherein data is further processed, analyzed and encrypted in a data processing module in an external unit.

The implant of any of the additional examples herein wherein data is downloaded to a smart phone or a tablet or a dedicated electronic device (e.g., the EID).

The implant of any of the additional examples herein wherein data is transmitted from an EID, a smart phone or a tablet to the computer of the caregiver.

The implant of any of the additional examples herein wherein data is transmitted by the caregiver to a remote data base.

An implant sized to be stabilized within an eye, the implant comprising an intraocular pressure sensor.

An implantable intraocular pressure sensor, comprising a pressure sensor and electronics coupled to the pressure sensor.

Any of the claimed implants, adapted to be positioned in any of the anatomical shows or described herein.

A method of positioning an intraocular pressure implant, comprising a sensor, in an eye.

A method of sensing intraocular pressure continuously, substantially continuously, or periodically, with an implantable intraocular sensor sized and configured to be stabilized within an eye.

Any of the claimed methods, further comprising transmitting information, either pressure data (e.g., raw or processed) or information indicative of pressure data wirelessly to an external device.

Any of the methods of calibrating an implantable pressure sensor herein.

A method of sensing pressure in an eye with an implantable device, wherein the implantable device is adapted to process the sensed pressure.

The implant of any of the additional examples herein wherein the implant comprises a memory module that further comprises non-erasable and/or reprogrammable memory elements.

The implant of any of the additional examples herein wherein the implant comprises a controller that controls its pressure sensing, data collection, processing, storage and transmission, and recharging operations.

The implant of any of the additional examples herein wherein a wireless connection between said implant and an external unit is operated at below 6 GHz, e.g., at 868 MHz, 900 MHz or 2.4 GHz.

The implant of any of the additional examples herein wherein the wireless connection between implant and external unit comprises electro-magnetic or inductive coupling between a transmitting and a receiving antenna.

The implant of any of the additional examples herein wherein the wireless connection between implant and external unit utilizes one or more antennas which can be e.g., straight, coiled, or flat.

The implant of any of the additional examples herein wherein the wireless connection between implant and external unit coupling has a system Q factor not less than 10 and not exceeding 100.

The implant of any of the additional examples herein wherein a transmitter coil transmits wireless power not exceeding 25 milliwatts.

The implant of any of the additional examples herein wherein recharging of the implant occurs at any distance between 2 cm and 2 meters.

The implant of any of the additional examples herein wherein preferred modes of charging the implant are either at 2-5 cm over 1 hour or 0.5-2.0 meters over 8 hours.

The implant of any of the additional examples herein wherein data is transmitted by the EID, the patient's smartphone or tablet to a remote data base.

The invention claimed is:

1. An implantable device with a biocompatible coating, comprising:
    a pressure sensing element; and
    a coating disposed on an outer surface of the implantable device, the coating comprising an inner layer disposed on the outer surface, and an exterior layer exposed to an ambient environment,
    wherein the inner layer has an inner cross link density, and the exterior layer has an exterior cross link density that is lower than the inner cross link density.

2. The implantable device of claim 1, wherein the exterior layer has an exterior refractive index and the inner layer has an inner refractive index greater than the exterior refractive index.

3. The implantable device of claim 1, wherein at least one of the exterior layer or the inner layer has a gradient refractive index, with the gradient refractive index being greater at an innermost location of the at least one of the exterior layer or the inner layer than at an outermost location of the at least one of the exterior layer or the inner layer.

4. The implantable device of claim 1, wherein the inner layer comprises at least one therapeutic agent that is adapted to be released from the inner layer.

5. The implantable device of claim 4, wherein the inner layer is configured to release the at least one therapeutic agent from the inner layer over a period of about 1 week to about 6 months after the implantable device is implanted into a mammalian body.

6. The implantable device of claim 5, further comprising an intermediate layer between the inner layer and the exterior layer,
wherein the intermediate layer is configured to act as a partial barrier to the release of the at least one therapeutic agent from the inner layer.

7. The implantable device of claim 4, wherein a first therapeutic agent of the at least one therapeutic agent inhibits expression of a cytokine in order to reduce adhesion of macrophages.

8. The implantable device of claim 7, wherein the cytokine is transforming growth factor beta (TGF-b).

9. The implantable device of claim 7, wherein the first therapeutic agent is Pirfenidone.

10. The implantable device of claim 4, wherein a first therapeutic agent of the at least one therapeutic agent is a steroid including at least one of dexamethasone or prednisolone.

11. The implantable device of claim 1, further comprising an intermediate layer between the inner layer and the exterior layer.

12. The implantable device of claim 11, wherein the intermediate layer has an intermediate cross link density that is different than the inner cross link density and the exterior cross link density.

13. The implantable device of claim 11, wherein each of the inner layer, the intermediate layer, and the exterior layer comprises a different polyethylene glycol based cross-linked network of different cross-link density and crystallinity.

14. The implantable device of claim 11, wherein the intermediate layer has a thickness that is less than an inner layer thickness and an exterior layer thickness.

15. The implantable device of claim 1, wherein the coating has a glass transition temperature in a range of −20° C. to +10° C. in a dehydrated state.

16. The implantable device of claim 1, wherein the coating has an elongation to break in a range of 30% to 250%.

17. The implantable device of claim 1, wherein the coating has a tensile modulus in a range of 0.01 to 5.0 MP.

18. The implantable device of claim 1, wherein the implantable device is configured to be fully implanted in a mammalian body.

19. The implantable device of claim 1, wherein the outer surface of the implantable device has at least one of a capsular shape or an ovoid shape.

20. The implantable device of claim 1, wherein the coating has a thickness of about 50 μm to about 200 μm.

* * * * *